(12) United States Patent
Gerbec et al.

(10) Patent No.: US 8,683,896 B2
(45) Date of Patent: Apr. 1, 2014

(54) ERGONOMIC SURGICAL INSTRUMENT HANDLE

(75) Inventors: Daniel E. Gerbec, Logan, UT (US); Joseph Q. Marietta, Hyde Park, UT (US); Brandon T. Walker, Layton, UT (US); E. Marlowe Goble, Logan, UT (US)

(73) Assignee: Medicine Lodge, Inc., Logan, UT (US)

( * ) Notice: Subject to any disclaimer, the term of this patent is extended or adjusted under 35 U.S.C. 154(b) by 346 days.

(21) Appl. No.: 13/041,846

(22) Filed: Mar. 7, 2011

(65) Prior Publication Data

US 2011/0218521 A1 Sep. 8, 2011

Related U.S. Application Data

(60) Provisional application No. 61/311,058, filed on Mar. 5, 2010, provisional application No. 61/373,385, filed on Aug. 13, 2010.

(51) Int. Cl.
*B25G 1/01* (2006.01)

(52) U.S. Cl.
USPC .................. 81/489; 81/320; 81/323; 81/329; 81/331

(58) Field of Classification Search
USPC .......................... 81/320, 323, 329, 331, 489
See application file for complete search history.

(56) References Cited

U.S. PATENT DOCUMENTS

| | | |
|---|---|---|
| D357,980 S | 5/1995 | Ek |
| D362,908 S | 10/1995 | Shutt |
| 6,117,158 A * | 9/2000 | Measamer et al. ............ 606/208 |
| 6,506,208 B2 * | 1/2003 | Hunt et al. ..................... 606/205 |
| 6,626,929 B1 | 9/2003 | Bannerman |
| 2007/0299469 A1 | 12/2007 | Carpenter |
| 2008/0009900 A1 | 1/2008 | Heaven |

* cited by examiner

*Primary Examiner* — Lee D Wilson
*Assistant Examiner* — Shantese McDonald
(74) *Attorney, Agent, or Firm* — Peter K. Johnson

(57) ABSTRACT

Instrument handles isolate the functions of supporting the instrument and actuating controls on the instrument. An instrument handle may be grasped and supported by the less dexterous digits and palm of a human hand, and controls mounted on the instrument handle may be actuated by the more dexterous digits. The instrument handle may couple to an end effector so that the hand, wrist, elbow, and shoulder remain in a comfortable position when the end effector is positioned to act effectively on a selected portion of a workpiece, such as a surgical site.

20 Claims, 29 Drawing Sheets

ERGONOMIC SURGICAL INSTRUMENT HANDLE

CROSS-REFERENCE TO RELATED APPLICATIONS

This application claims the benefit of the filing date of:

U.S. Provisional Patent Application No. 61/311,058, which was filed on Mar. 5, 2010, is entitled ERGONOMIC SURGICAL INSTRUMENT HANDLE. The contents of U.S. Application No. 61/311,058 are hereby incorporated by reference as part of this application.

This application also claims the benefit of the filing date of:

U.S. Provisional Patent Application No. 61/373,385, which was filed on Aug. 13, 2010, is entitled ERGONOMIC SURGICAL INSTRUMENT HANDLE. The contents of U.S. Application No. 61/373,385 are hereby incorporated by reference as part of this application.

BACKGROUND OF THE INVENTION

The present disclosure relates to handle designs for improved stability, comfort, and control. While the present disclosure is made in the context of handles for surgical instruments, such as arthroscopic, laparoscopic, endoscopic, minimally invasive instruments, or other instruments, among others, the principles embodied in the present disclosure may be applicable outside the fields of surgery or medical devices.

Most manually actuated instruments used in the areas of arthroscopic or laparoscopic surgery are supported, or grounded, by the thumb and one or more of the fingers of a user's hand. Typically, such instruments are supported by inserting the thumb through a loop on a rear handle, which may be a stationary handle, and inserting one or more fingers through a loop on a front handle, which may be a movable handle. These instruments are often actuated by opening or closing the opposing handles with the thumb and finger(s) of the working hand. Such an arrangement may make it difficult to keep a working tip, or end effector, of the instrument stabilized at a precise location relative to a patient's anatomy, because the fingers that must stabilize the end effector are the same ones that must move to actuate the end effector. It can be difficult or fatiguing for a user to adequately compensate for actuation movement in such an arrangement.

Many manually actuated arthroscopic or laparoscopic instruments are designed as a set of several instruments, all with a consistent handle design and a consistent orientation between the handle and the end effector for all instruments in the set. Some instrument sets vary the end effector orientation by including some up- or down-angle end effectors. However, users may find themselves routinely adopting uncomfortable or injurious postures in order to simultaneously position an end effector in a desired orientation relative to a patient's anatomy, and position the hand to actuate the end effector. Occupational exposure to exaggerated postures may result in long term effects to the user, and have the potential to limit the efficacy of the instruments used.

There is a need for instrument handles that isolate the functions of supporting the instrument and actuating the instrument. There is a need for a set of instrument handles, working shafts, or both, that provides different orientations between the user's hand and the end effector, so that a user may select from the set a handle and/or shaft that positions the end effector appropriately for a given application while permitting a comfortable, safe working posture.

SUMMARY OF THE INVENTION

The present disclosure sets forth instrument handles that isolate the functions of supporting the instrument and actuating the instrument. In many of the disclosed embodiments, the handle may be stabilized by less dexterous portions of the hand, thus leaving more dexterous portions of the hand free to actuate the instrument. In some embodiments, the handle may be stabilized by the ulnar three fingers (middle, ring, and little fingers) and the palm or base of the thumb (thenar eminence), and may be actuated by the index finger and/or thumb.

The present disclosure sets forth instrument handles that provide different orientations between the user's hand and the end effector. These handles permit the user to keep their shoulder, elbow, wrist, and hand in an ergonomically neutral position for a wide variety of end effector orientations.

An ergonomically neutral position or posture minimizes stress and fatigue on muscles and joints during activity, thereby reducing the possibility of neuromuscular disorders or repetitive strain injuries to the body part or parts. A posture in which the upper arm hangs relaxed from the shoulder with the hands, wrists, and forearms straight, in-line and roughly parallel to the floor may be described as an ergonomically neutral position. The forearms may be rotated so that the thumbs are slightly elevated relative to the little fingers.

In some embodiments of the present disclosure, a shaft may extend from the handle in line with the user's forearm. In other embodiments, the shaft may extend from the handle obliquely relative to the forearm. In still other embodiments, the shaft may be bent, curved, or twisted. In some embodiments, the handle may sit more squarely in the hand and in other embodiments, the handle may be more inclined within the hand. Some embodiments position the working shaft of the instrument beside the index finger, while others position the working shaft of the instrument between the index and middle fingers. Each of these embodiments may permit the user to keep their shoulder, elbow, wrist, and hand in an economically neutral position for a particular end effector orientation.

DETAILED DESCRIPTION

Figure 1A:
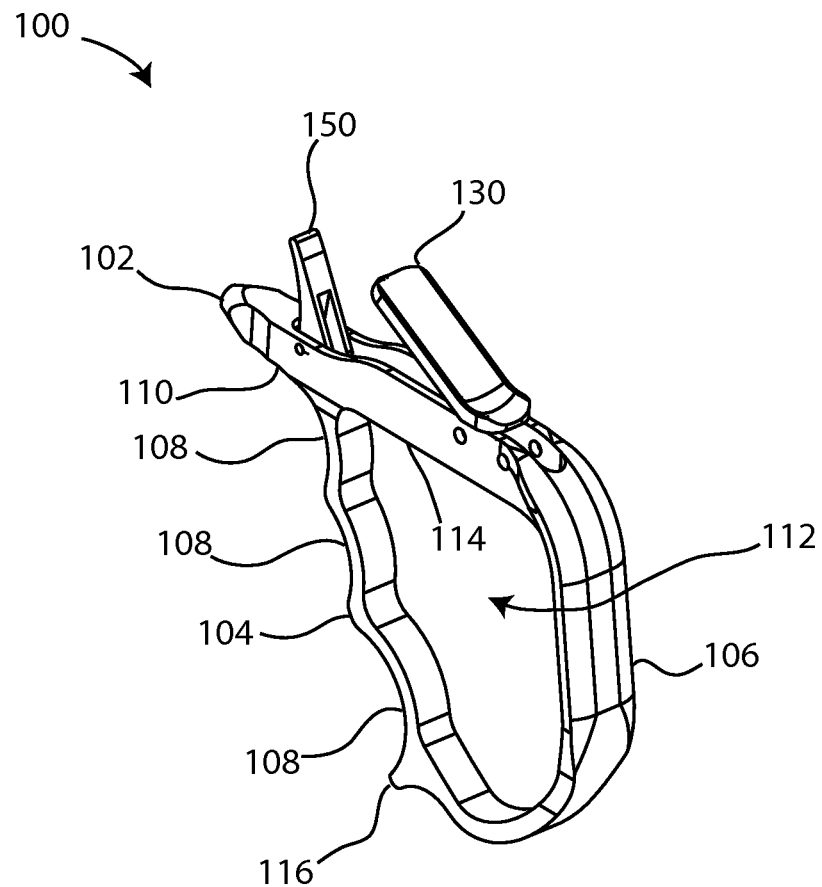
FIG. 1A is a side perspective view of an instrument handle.

While certain embodiments have been shown and described in detail below, it will be clear to the person skilled in the art upon reading and understanding this disclosure that changes, modifications, and variations may be made and remain within the scope of the systems, kits, components, and methods described herein. Furthermore, while various features are grouped together in the embodiments for the purpose of streamlining the disclosure, it is appreciated that features from different embodiments may be combined to form additional embodiments which are all contemplated within the scope of the present disclosure.

The following description and accompanying drawings are offered by way of illustration only. In particular, while the present disclosure sets forth an embodiment in the context of handles for surgical instruments, one of skill in the art will appreciate that the components, systems, kits, and methods may be applicable to handles in other fields.

Not every feature of each embodiment is labeled in every figure in which that embodiment appears, in order to keep the figures clear. Similar reference numbers (for example, those that are identical except for the first numeral) are used to indicate similar features in different embodiments.

Standard medical planes of reference and descriptive terminology are employed in this specification. A sagittal plane divides a body into right and left portions. A mid-sagittal plane divides the body into equal right and left halves. A coronal plane divides a body into anterior and posterior portions. A transverse plane divides a body into superior and inferior portions. Anterior means toward the front of the body. Posterior means toward the back of the body. Superior means toward the head. Inferior means toward the feet. Medial means toward the midline of the body. Lateral means away from the midline of the body. Axial means toward a central axis of the body. Abaxial means away from a central axis of the body. These descriptive terms may be applied to an animate or inanimate body. Ipsilateral means on the same side of the body. Contralateral means on the opposite side of the body.

Referring to FIGS. 1A-5, an instrument handle 100 may include a frame 110, a first control 130, and a second control 150. Handle 100 may be bilaterally symmetric about a mid-sagittal plane 101. Referring to FIGS. 1B-1D, handle 100 may be operatively assembled to an operative component 10 to form a complete surgical instrument. Handle 100 may be permanently or releasably coupled to operative component 10. Handle 100 may couple to any one of a plurality of different operative components 10.

Frame 110 may include a fitting 102, a body portion 114, a finger portion 104, and a palm portion 106. Body portion 114, finger portion 104, and palm portion 106 may be arranged around three sides of frame 110. Frame 110 may be bilaterally symmetric about the mid-sagittal plane 101 of handle 100. Furthermore, fitting 102, body portion 114, finger portion 104, and palm portion 106 may each be bilaterally symmetric about the mid-sagittal plane 101 of handle 100.

Fitting 102 may be described as a docking feature or connection feature to connect handle 100 to operative component 10. For example, fitting 102 may be a socket, as shown in FIGS. 1A-5, a through hole, or a protrusion.

Body portion 114 may be described as a portion of the frame 110 which supports fitting 102, first control 130, and second control 150. Fitting 102 may be carried on a front segment of body portion 114, as illustrated. Body portion 114 may extend generally in line with fitting 102. However, body portion 114 may extend in another orientation relative to fitting 102, such as oblique or transverse, in order to position a shaft 14 of an operative component 10 in a desired orientation relative to a user's hand. In other words, the orientation between body portion 114 and fitting 102 may set an orientation between the mid-sagittal plane 101 and a center longitudinal axis of the shaft 14. The center longitudinal axis may lie in the mid-sagittal plane 101 in line with the body portion 114 or at an angle to body portion 114. The center longitudinal axis may lie parallel to, and offset from, the mid-sagittal plane 101. The center longitudinal axis may lie at an angle to the mid-sagittal plane 101 so that the center longitudinal axis intersects the mid-sagittal plane 101.

Finger portion 104 may be described as a portion of the frame 110 for contacting one or more of the fingers of a human hand. Finger portion 104 may extend transversely from body portion 114, and may be located close to fitting 102. Finger portion 104 may include one or more indentations 108. FIGS. 1A-5 illustrate three indentations 108 which are sized, shaped, and positioned to fit the ulnar three fingers of a human hand. Finger portion 104 may also include one or more finger rests 116. FIGS. 1A-5 illustrate a finger rest 116 which is sized, shaped, and positioned to fit the outer side of the little finger. The indentations 108 and/or finger rests 116 may increase the accuracy or security with which a user can grasp handle 100.

Palm portion 106 may be described as a portion of the frame 110 for contacting the palm of a human hand. For example, palm portion 106 may contact the palm or thenar eminence of a human hand. Palm portion 106 may extend transversely from a rear segment of body portion 114 opposite the front segment, as illustrated, and thus may be located at a distance from fitting 102. Palm portion 106 may blend smoothly with body portion 114. Palm portion 106 may also connect to finger portion 104 at a distance from body portion 114, and may blend smoothly with finger portion 104.

Frame 110 may include one or more apertures 112 between body portion 114, finger portion 104, and palm portion 106. The embodiment of FIGS. 1A-5 is shown with a large aperture 112 which hollows out a central portion of frame 110 so that body portion 114, finger portion 104, and palm portion 106 form a continuous perimeter around aperture 112. The apertures 112 may reduce the mass of frame 110, making the handle 100 lighter and easier to use for long periods of time. Reducing mass may decrease manufacturing costs by reducing the amount of material required to fabricate frame 110.

First control 130 may be described as an actuator for a first action or first mechanism of a surgical instrument. First control 130 may actuate a mechanical linkage within handle 100 and/or operative component 10. For example, first control 130 may actuate a mechanism that pushes, pulls, or rotates at least a portion of the surgical instrument, such as a portion of an inner or outer shaft of the operative component 10, or an end effector 12. First control 130 may alternatively energize an electrical circuit within handle 100 and/or operative component 10. The electrical circuit may provide a direct effect such as radio frequency ablation, cautery, imaging, ultrasonics, global positioning system (GPS), or electrical stimulation, among others. The electrical circuit may alternatively be coupled to a mechanical or electro-mechanical mechanism which provides a direct effect. First control 130 may alternatively energize a hydraulic circuit, such as suction or irrigation, among others. Some examples of a first control 130 are a lever, a button, a trigger, a toggle, a slider, a knob, a dial, a wheel, a plunger, or a switch. First control 130 may be biased to remain in a default, or normal, position unless actively actuated by a user. First control 130 may alternatively remain in the last selected position or setting until actuated by the user to another position or setting. First control 130 may include a plurality of settings. For example, first control 130 may be a three-position sliding switch, or a knob that can be turned to any desired rotational setting. First control 130 may be subdivided into separate portions, each portion controlling a corresponding one of the plurality of settings. For example, first control 130 may comprise a first button stacked over a second button, so that pressing the first button lightly actuates a first mechanism, and pressing the first button more heavily depresses the second button, actuating a second mechanism. In another example, first control 130 may be divided into left and right halves, each half independently operable. First control 130 may be at least partially integrally formed with frame 110, or may be formed as a separate part and assembled to frame 110. FIGS. 1A-5 illustrate a first control 130 which is a spring biased lever or trigger that protrudes obliquely from the body portion 114 opposite the finger and palm portions 104, 106 at a distance from the fitting 102. The illustrated first control 130 is hinged to the body portion 114 near the blend with palm portion 106 and is spring biased away from the body portion 114. The illustrated first control 130 is actuated by pressing the first control 130 toward the body portion 114, and automatically returns to the illustrated position when released.

Second control 150 may be described as an actuator for a second action or a second mechanism of a surgical instrument. Second control 150 may share one, some, or all of the characteristics set forth for first control 130. Second control 150 may embody a different subset of characteristics than first control 130. FIGS. 1A-5 illustrate a second control 150 which is a spring biased lever or trigger that protrudes transversely from the body portion 114 opposite the finger and palm portions 104, 106 near the fitting 102. The illustrated second control 150 is hinged to the body portion 114 near the finger portion 104 and is spring biased toward the fitting 102. The illustrated second control 150 is actuated by pulling the second control 150 away from the fitting 102 with the index finger, and automatically returns to the illustrated position when released.

Figure 1B:
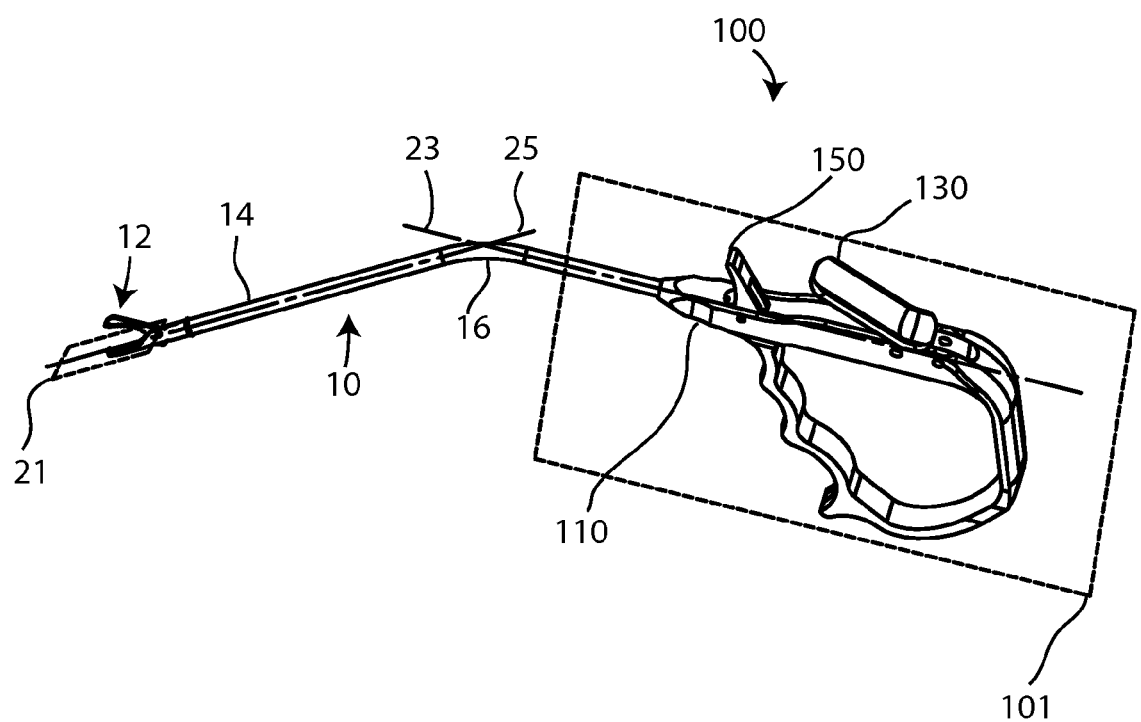
FIG. 1B is a top perspective view of the handle of FIG. 1A operatively assembled with an operative component.
Figure 1C:
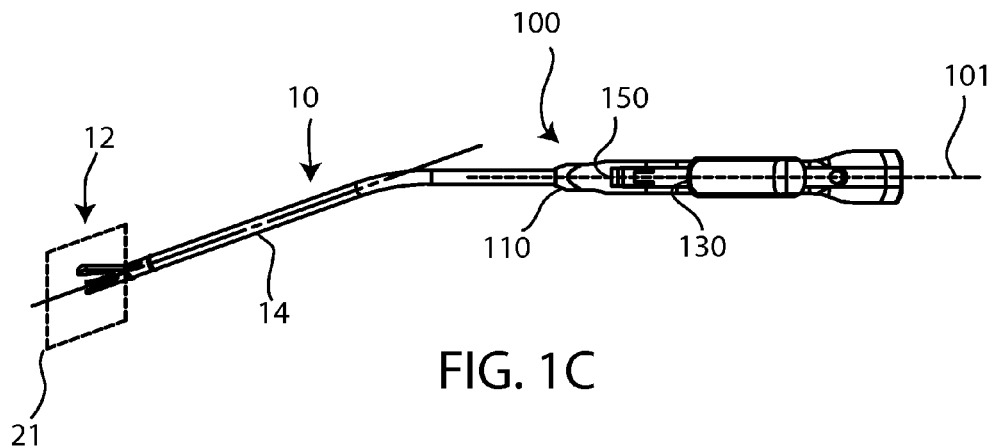
FIG. 1C is a top view of the handle and operative component of FIG. 1B.
Figure 1D:
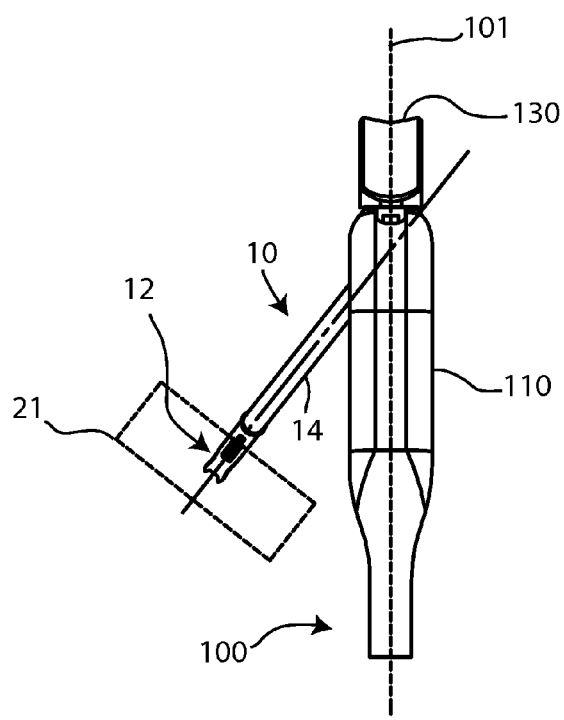
FIG. 1D is a right view of the handle and operative component of FIG. 1B.
Figure 2:
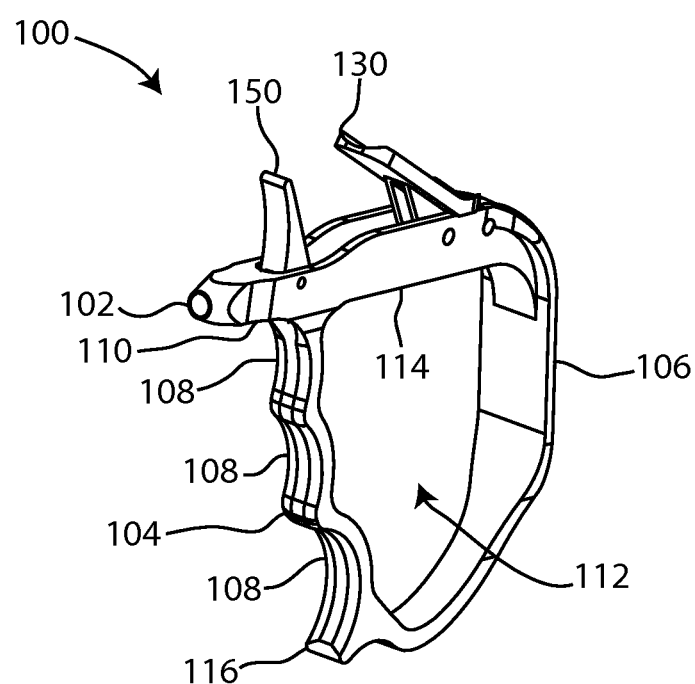
FIG. 2 is another side perspective view of the handle of FIG. 1A.
Figure 3:
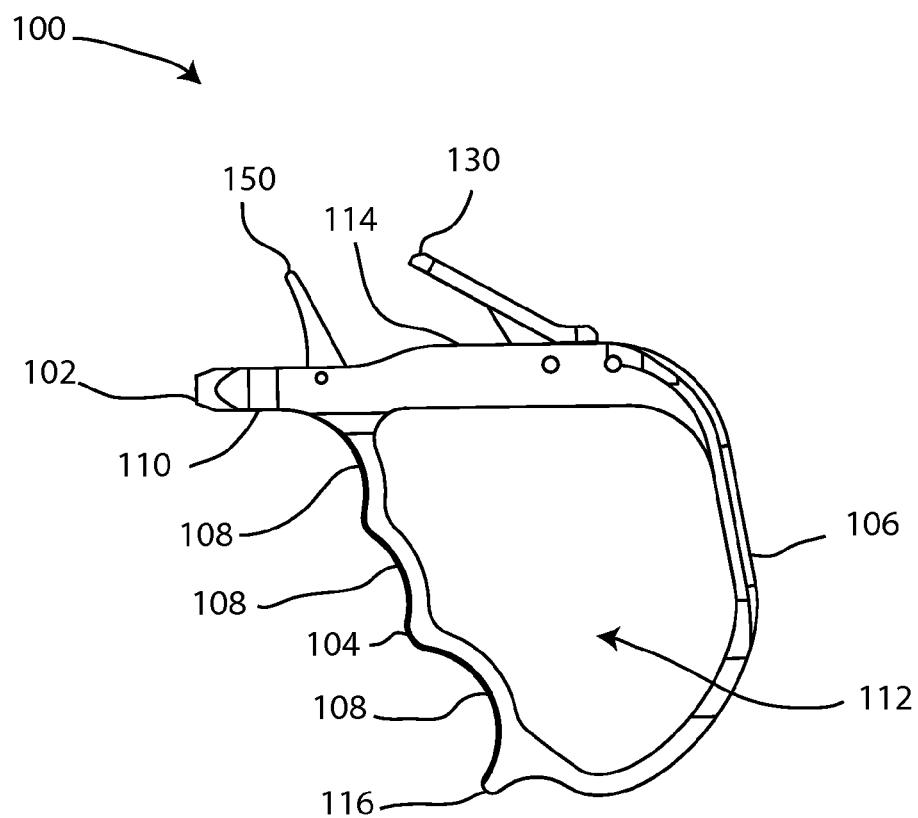
FIG. 3 is a side view of the handle of FIG. 1A.
Figure 4:
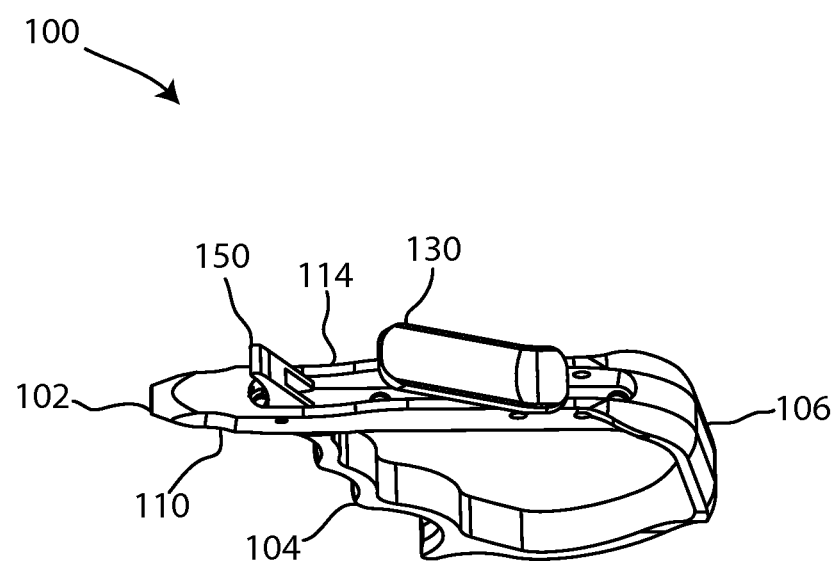
FIG. 4 is a top perspective view of the handle of FIG. 1A.
Figure 5:
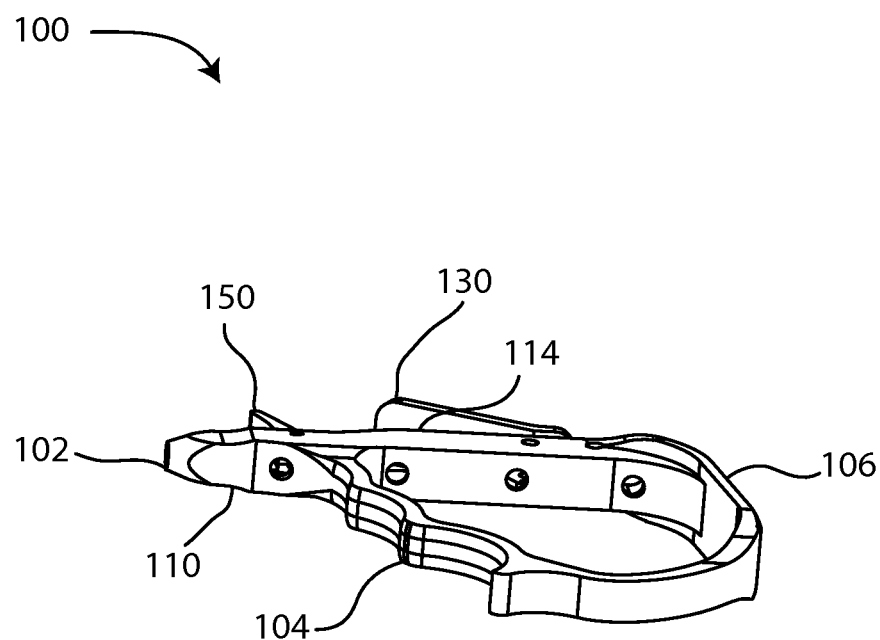
FIG. 5 is a bottom perspective view of the handle of FIG. 1A.
Figure 6:
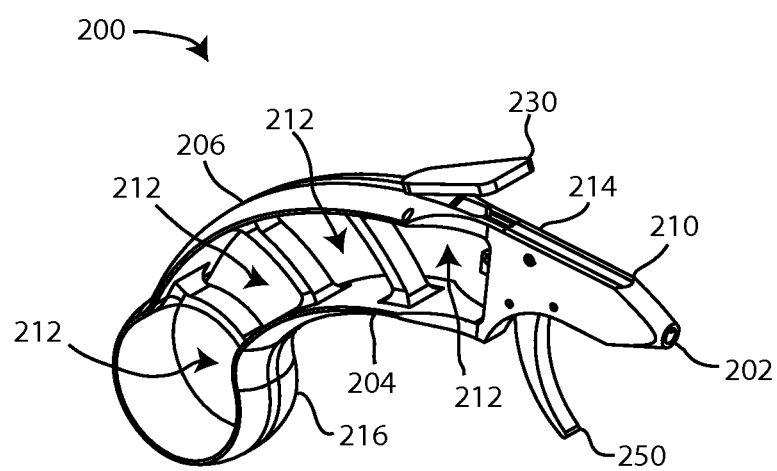
FIG. 6 is a side perspective view of another instrument handle.
Figure 7:
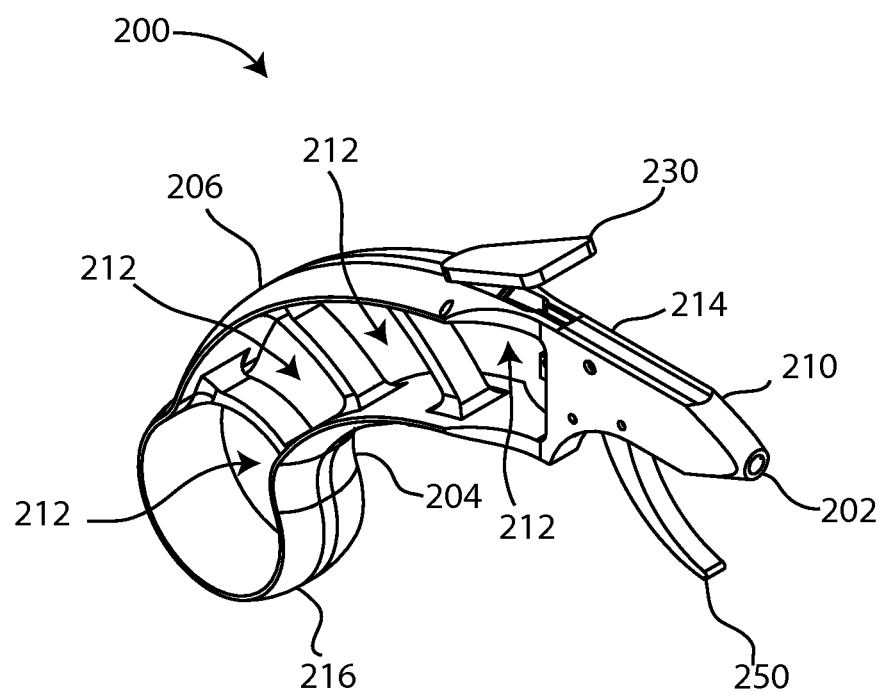
FIG. 7 is a side perspective view of the handle of FIG. 6.
Figure 8:
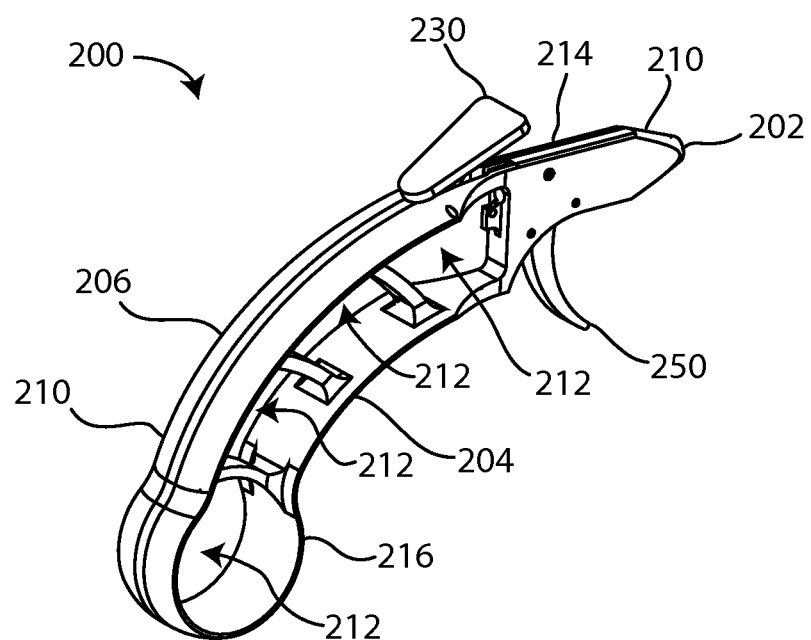
FIG. 8 is another side perspective view of the handle of FIG. 6.
Figure 9:
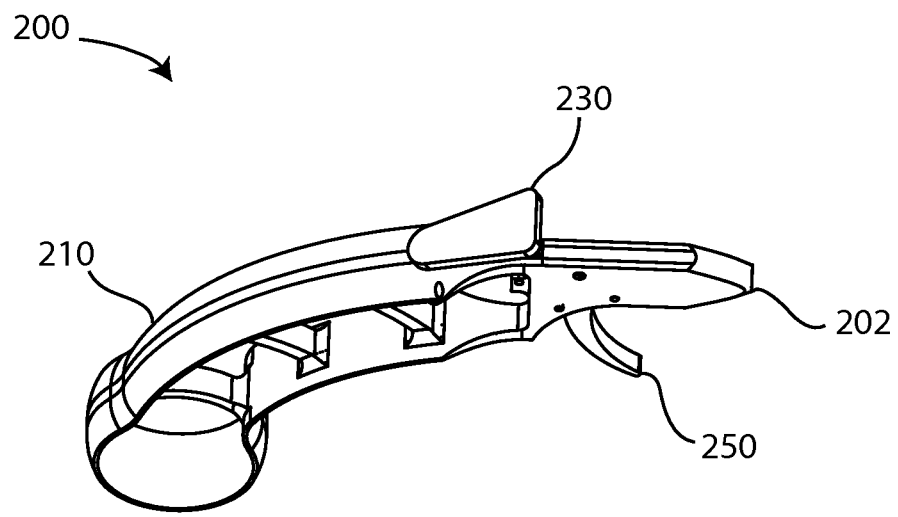
FIG. 9 is a top perspective view of the handle of FIG. 6.
Figure 10:
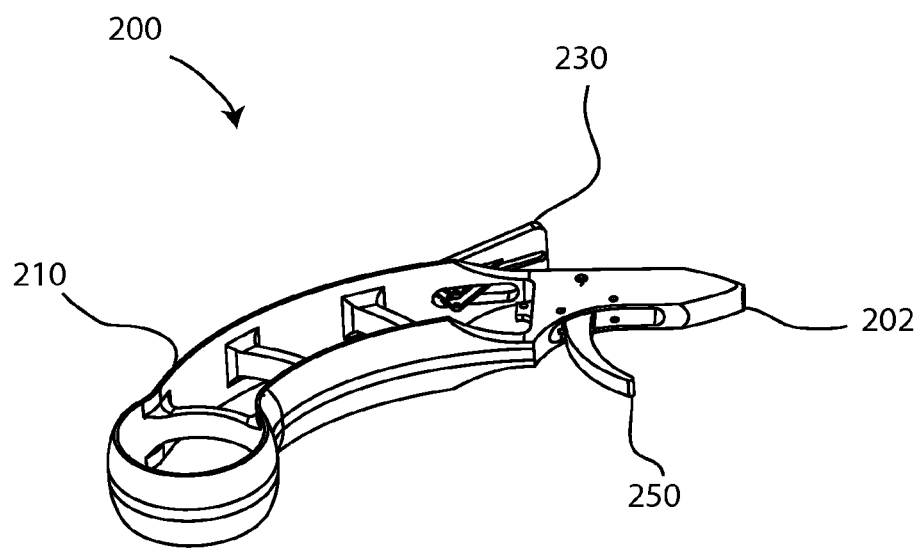
FIG. 10 is a bottom perspective view of the handle of FIG. 6.

Referring to FIGS. 1B-1D, operative component 10 includes a working segment, or an end effector 12 which performs one or more actions, such as a surgical function. For example, end effector 12 may bite, grasp, shear, cut, lift, poke, and/or punch. In these examples, end effector 12 may be described as a biter, a grasper, a scissors, a side cutter, an awl, and/or a punch. Operative component 10 may also be generally referred to as an end effector. For each of the examples, end effector 12 may have a functional plane 21 which relates to the direction of action of the end effector 12. For example, an end effector 12 with jaws may have a functional plane 21 where the jaws touch when closed. In another example, a cutting end effector 12 may have a functional plane 21 that intersects a cutting edge of the end effector 12. In yet another example, an end effector 12 with a rotating side-cutting burr inside a windowed outer housing may have a functional plane 21 through the axis of rotation of the burr and bisecting the window. Alternately, a functional plane 21 may lie across the window.

End effector 12 may be mounted on a shaft 14 to position the end effector 12 a desired distance away from handle 100 when operative component 10 is operatively assembled with handle 100. For example, shaft 14 may be long enough to pass through a surgical cannula and across a full width of a joint space. Shaft 14 may also include one or more bends, curves, or twists 16 in order to position end effector 12 in a desired orientation relative to the surgical anatomy when handle 100 is held in a physiologically neutral position. Shaft 14 may include a center longitudinal axis 23 relating to an end of the shaft 14 opposite the end effector 12; if bent, shaft 14 may include additional center longitudinal axes 25 relating to each additional portion of the shaft 14. The end of the shaft 14 opposite the end effector 12 may be described as a connection segment because it can serve to connect end effector 12 to handle 100. FIGS. 1B-1C illustrate an operative component 10 with an end effector 12 configured as a grasper. In the illustrated example, the functional plane 21 is a plane at which the grasper jaws meet when closed. In the illustrated example, the shaft 14 is straight except for bend 16, thus shaft 14 has an axis 23 and an additional axis 25.

It can be appreciated from FIGS. 1B-D that the plane 21 lies at a compound angle to plane 101 in the illustrated example. This may be best seen in FIGS. 1C-D, where plane 21 is at a first angle to plane 101 when viewed from the top (FIG. 1C), and at a second angle to plane 101 when viewed from the right (FIG. 1D). In other examples, however, the functional plane 21 may be at some other orientation, such as a single angle, parallel, or coplanar. By orienting the functional plane 21 as required to reach the relevant anatomy, while orienting the mid-sagittal plane 101 of the handle 100 as required to maintain a neutral wrist, elbow, and arm position, the handles and systems of the present disclosure reduce the need for a user to endure uncomfortable and potentially harmful postures.

In use, handle 100 may be grasped by a human hand so that the palm portion 106 rests against the palm or thenar eminence; the finger portion 104 rests against the middle, ring, and little fingers with the little finger in an indentation 108 adjacent to the finger rest 116, the middle finger in an indentation 108 adjacent to the fitting 102, and the ring finger in an indentation 108 between the middle and little fingers; the thumb rests on the first control 130; the index finger rests on the second control 150; and the fitting 102 is positioned between the index and middle fingers so that a shaft 14 of an operative component may extend between the index and middle fingers. In use, handle 100 is supported between the palm or thenar eminence and the middle, ring, and little fingers so that the thumb and index finger are free to operate the first and second controls 130, 150 respectively. Furthermore, it can be appreciated that, in use, handle 100 is completely contained within the user's hand so that there is no projecting hardware other than the operative component 10.

Handle 100 may rest in a user's hand in a square orientation so that the shaft 14 extends from the handle 100 generally parallel to the forearm of the user. The illustrated handle 100 may be suited to situations in which the end effector 12 approaches the anatomy straight on. In other examples of handle 100, shaft 14 may extend obliquely or transversely relative to the forearm, as established by the orientation of body portion 114 to fitting 102.

Operative component 10 may be advantageously stabilized and controlled when the shaft 14 is between the index and middle fingers. When the shaft 14 is between the index and middle fingers, the wrist becomes the primary joint for biomechanical control of the end effector 12, and motion at the elbow and shoulder may be unnecessary.

Referring to FIGS. 6-10, an instrument handle 200 may include a frame 210, a first control 230, and a second control 250. Handle 200 may be bilaterally symmetric about a mid-sagittal plane like handle 100. Handle 200 may be operatively assembled to an operative component 10 to form a complete surgical instrument like handle 100. Handle 200 may be permanently or releasably coupled to operative component 10. Handle 200 may couple to any one of a plurality of different operative components 10.

Frame 210 may include a fitting 202, a body portion 214, a finger portion 204, and a palm portion 206. Body portion 214, finger portion 204, and palm portion 206 may be arranged around three sides of frame 210. Frame 210 may be bilaterally symmetric about the mid-sagittal plane of handle 200. Furthermore, fitting 202, body portion 214, finger portion 204, and palm portion 206 may each be bilaterally symmetric about the mid-sagittal plane of handle 200.

Fitting 202 may be described as a docking feature or connection feature to connect handle 200 to operative component 10. For example, fitting 202 may be a socket, as shown in FIGS. 6-10, a through hole, or a protrusion.

Body portion 214 may be described as a portion of the frame 210 which supports fitting 202, first control 230, and second control 250. Fitting 202 may be carried on a front segment of body portion 214, as illustrated. Body portion 214 may extend generally in line with fitting 202. However, body portion 214 may extend in another orientation relative to fitting 202, such as oblique or transverse, in order to position a shaft 14 of an operative component 10 in a desired orientation relative to a user's hand, as described for handle 100.

Finger portion 204 may be described as a portion of the frame 210 for contacting one or more of the fingers of a human hand. Finger portion 204 may extend obliquely from body portion 214 opposite fitting 202. Finger portion 204 may include one or more indentations like handle 100. However, FIGS. 6-10 illustrate a finger portion 204 which is smooth, broad, and gently rounded. Finger portion 204 may also include one or more finger rests 216. FIGS. 6-10 illustrate a finger rest 216 which is sized, shaped, and positioned to fit the outer side of the little finger. The illustrated example of finger rest 216 is formed as an enlarged partial loop. The indentations and/or finger rests 216 may increase the accuracy or security with which a user can grasp handle 200.

Palm portion 206 may be described as a portion of the frame 210 for contacting the palm of a human hand. For example, palm portion 206 may contact the palm or thenar eminence of a human hand. Palm portion 206 may extend obliquely from body portion 214 opposite fitting 202 and generally parallel to finger portion 204. Palm portion 206 may blend smoothly with body portion 214. Palm portion 206 may also blend smoothly into finger rest 216.

Frame 210 may include one or more apertures 212 between body portion 214, finger portion 204, and palm portion 206. The embodiment of FIGS. 6-10 is shown with four large apertures 212 which hollow out a central portion of frame 210 so that body portion 214, finger portion 204, and palm portion 206 form a continuous perimeter around the apertures 212. The apertures 212 may reduce the mass of frame 210, making the handle 200 lighter and easier to use for long periods of time. Reducing mass may decrease manufacturing costs by reducing the amount of material required to fabricate frame 210.

First control 230 and second control 250 may be described as actuators for first and second mechanisms, respectively, of a surgical instrument. First and second controls 230, 250 may share one, some, or all of the characteristics set forth for first control 130. First and second controls 230, 250 may embody different subsets of characteristics than first control 130. FIGS. 6-10 illustrate examples of first and second controls 230, 250. The illustrated first control 230 is a spring biased lever or trigger that protrudes obliquely from the body portion 214 opposite the finger portion 204 and at a distance from the fitting 202. The illustrated first control 230 is hinged to the body portion 214 near the blend with palm portion 206 and is spring biased away from the body portion 214. The illustrated first control 230 is actuated by pressing the first control 230 toward the body portion 214, and automatically returns to the illustrated position when released. The illustrated second control 250 is a spring biased lever or trigger that protrudes transversely from the body portion 214 opposite first control 230 and at a distance from the fitting 202. The illustrated second control 250 and the finger portion 204 are on the same side of the fitting 202. The illustrated second control 250 is hinged to the body portion 214 and is spring biased toward the fitting 102. The illustrated second control 250 is actuated by pulling the second control 250 away from the fitting 202 with the index finger, and automatically returns to the illustrated position when released.

In use, handle 200 may be grasped by a human hand so that the palm portion 206 rests against the palm or thenar eminence; the finger portion 204 rests against the middle, ring, and little fingers with the little finger adjacent to the finger rest 216; the thumb rests on the first control 230; the index finger rests on the second control 250; and the fitting 202 is positioned beside the index finger so that a shaft 14 of an operative component may extend beside the index finger. In use, handle 200 is supported between the palm or thenar eminence and the middle, ring, and little fingers so that the thumb and index finger are free to operate the first and second controls 230, 250. Furthermore, it can be appreciated that, in use, handle 200 is completely contained within the user's hand so that there is no projecting hardware other than the operative component 10.

Handle 200 may rest in a user's hand in a forwardly-inclined orientation so that the shaft 14 extends from the handle 200 generally parallel to the forearm of the user. The illustrated handle 200 may also be suited to situations where the end effector 12 approaches the anatomy from below. In other examples of handle 200, shaft 14 may extend obliquely or transversely relative to the forearm, as established by the orientation of body portion 214 to fitting 202. It can also be appreciated that handle 200 may be favorably adapted for a user having a smaller grip span.

Figure 11:
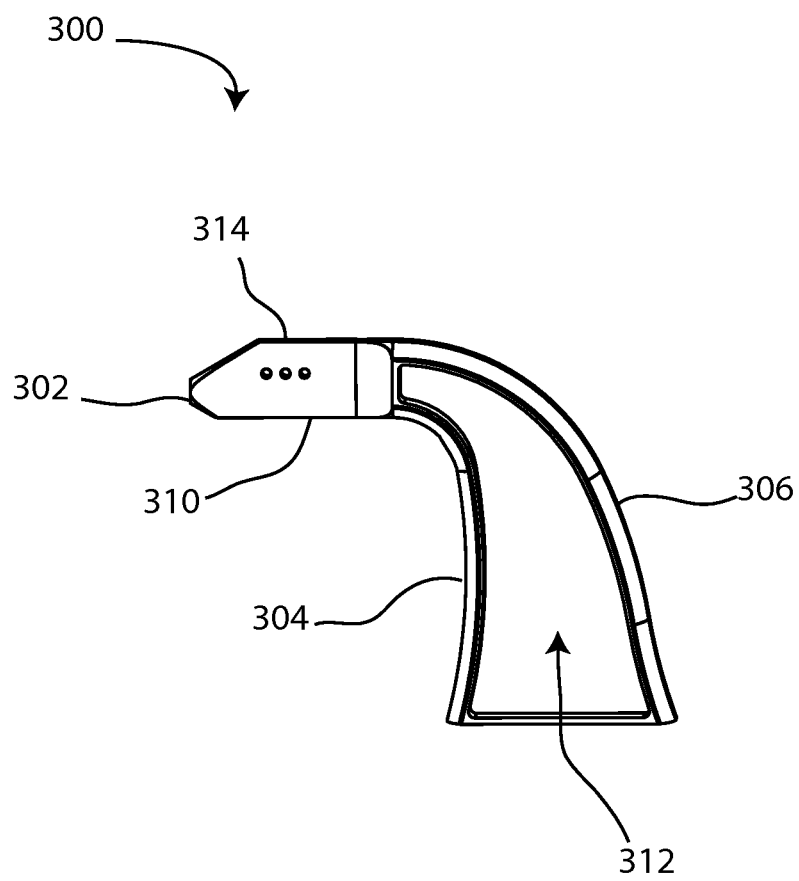
FIG. 11 is a side view of yet another instrument handle.
Figure 12:
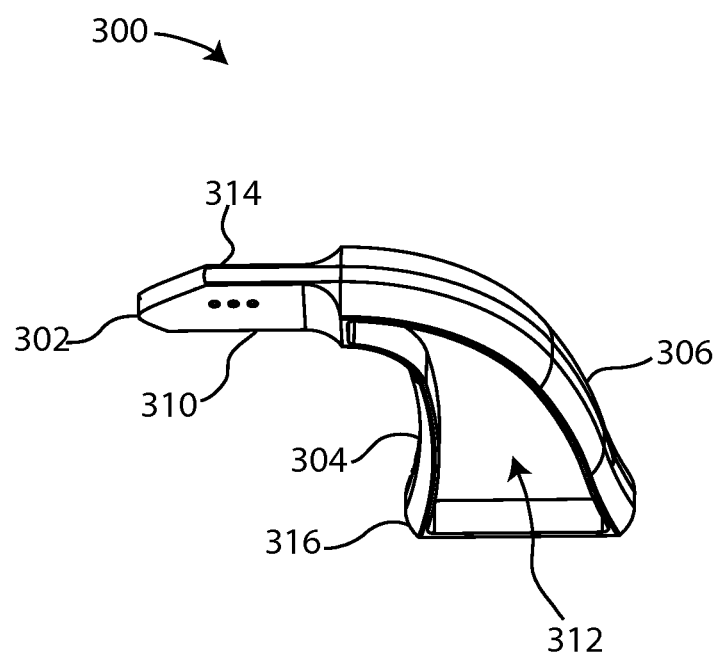
FIG. 12 is a top perspective view of the handle of FIG. 11.

Referring to FIGS. 11-12, an instrument handle 300 may include a frame 310. Handle 300 may be bilaterally symmetric about a mid-sagittal plane like handle 100. Handle 300 may be operatively assembled to an operative component 10 to form a complete surgical instrument like handle 100. Handle 300 may be permanently or releasably coupled to operative component 10. Handle 300 may couple to any one of a plurality of different operative components 10.

Frame 310 may include a fitting 302, a body portion 314, a finger portion 304, and a palm portion 306. Body portion 314, finger portion 304, and palm portion 306 may be arranged around three sides of frame 310. Frame 310 may be bilaterally symmetric about the mid-sagittal plane of handle 300. Furthermore, fitting 302, body portion 314, finger portion 304, and palm portion 306 may each be bilaterally symmetric about the mid-sagittal plane of handle 300.

Fitting 302 may be described as a docking feature or connection feature to connect handle 300 to operative component 10. For example, fitting 302 may be a socket, a through hole, or a protrusion.

Body portion 314 may be described as a portion of the frame 310 which supports fitting 302. Body portion 314 may extend generally in line with fitting 302. However, body portion 314 may extend in another orientation relative to fitting 302, such as oblique or transverse, in order to position a shaft 14 of an operative component 10 in a desired orientation relative to a user's hand, as described for handle 100.

Finger portion 304 may be described as a portion of the frame 310 for contacting one or more of the fingers of a human hand. Finger portion 304 may extend obliquely from body portion 314 opposite fitting 302. Finger portion 304 may include one or more indentations like handle 100. However, FIGS. 11-12 illustrate a finger portion 304 which is smooth, broad, and gently rounded. Finger portion 304 may also include one or more finger rests 316. FIGS. 11-12 illustrate a finger rest 316 which is sized, shaped, and positioned to fit the outer side of the little finger. The indentations and/or finger rests 316 may increase the accuracy or security with which a user can grasp handle 300.

Palm portion 306 may be described as a portion of the frame 310 for contacting the palm of a human hand. For example, palm portion 306 may contact the palm or thenar eminence of a human hand. Palm portion 306 may extend obliquely from body portion 314 opposite fitting 302 and generally parallel to finger portion 304. Palm portion 306 may blend smoothly with body portion 314. Palm portion 306 may connect to finger portion 304 opposite body portion 314.

Frame 310 may include one or more apertures 312 between body portion 314, finger portion 304, and palm portion 306. The embodiment of FIGS. 11-12 is shown with a large aperture 312 which hollows out a central portion of frame 310 so that body portion 314, finger portion 304, and palm portion 306 form a continuous perimeter around the aperture 312. The aperture 312 may reduce the mass of frame 310, making the handle 300 lighter and easier to use for long periods of time. Reducing mass may decrease manufacturing costs by reducing the amount of material required to fabricate frame 310.

In use, handle 300 may be grasped by a human hand so that the palm portion 306 rests against the palm or thenar eminence; the finger portion 304 rests against the middle, ring, and little fingers with the little finger adjacent to the finger rest 316; and the fitting 302 is positioned beside the index finger so that a shaft 14 of an operative component may extend beside the index finger. In use, handle 300 is supported between the palm or thenar eminence and the middle, ring, and little fingers. Furthermore, it can be appreciated that, in use, handle 300 is completely contained within the user's hand so that there is no projecting hardware other than the operative component 10.

Handle 300 may rest in a user's hand in an orientation that allows shaft 14 to extend from the handle 300 generally parallel to the forearm of the user. The illustrated handle 300 may be suited to situations in which the end effector 12 approaches the anatomy straight on. In other examples of handle 300, shaft 14 may extend obliquely or transversely relative to the forearm, as established by the orientation of body portion 314 to fitting 302.

Figure 13:
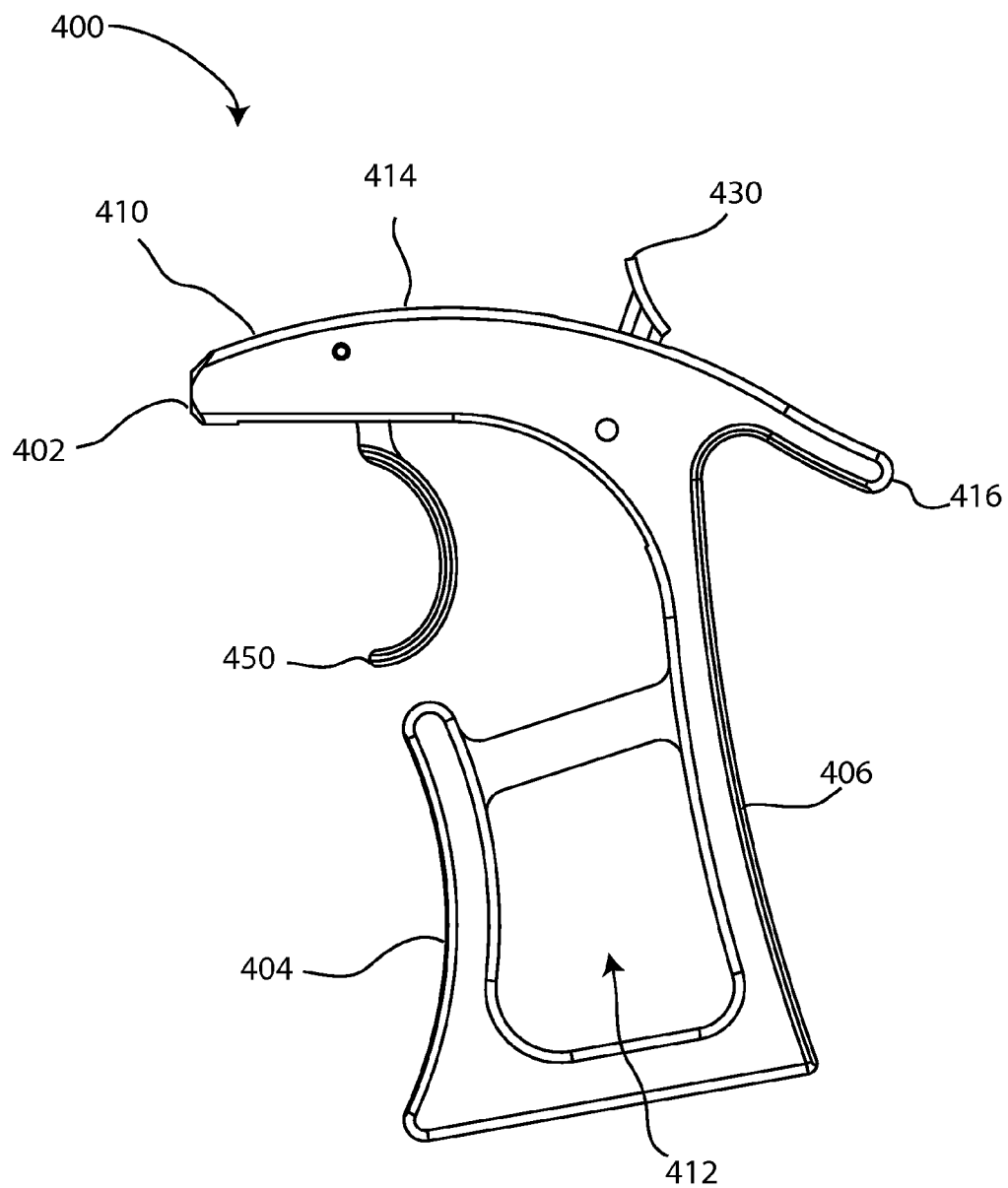
FIG. 13 is a side view of yet another instrument handle.
Figure 14:
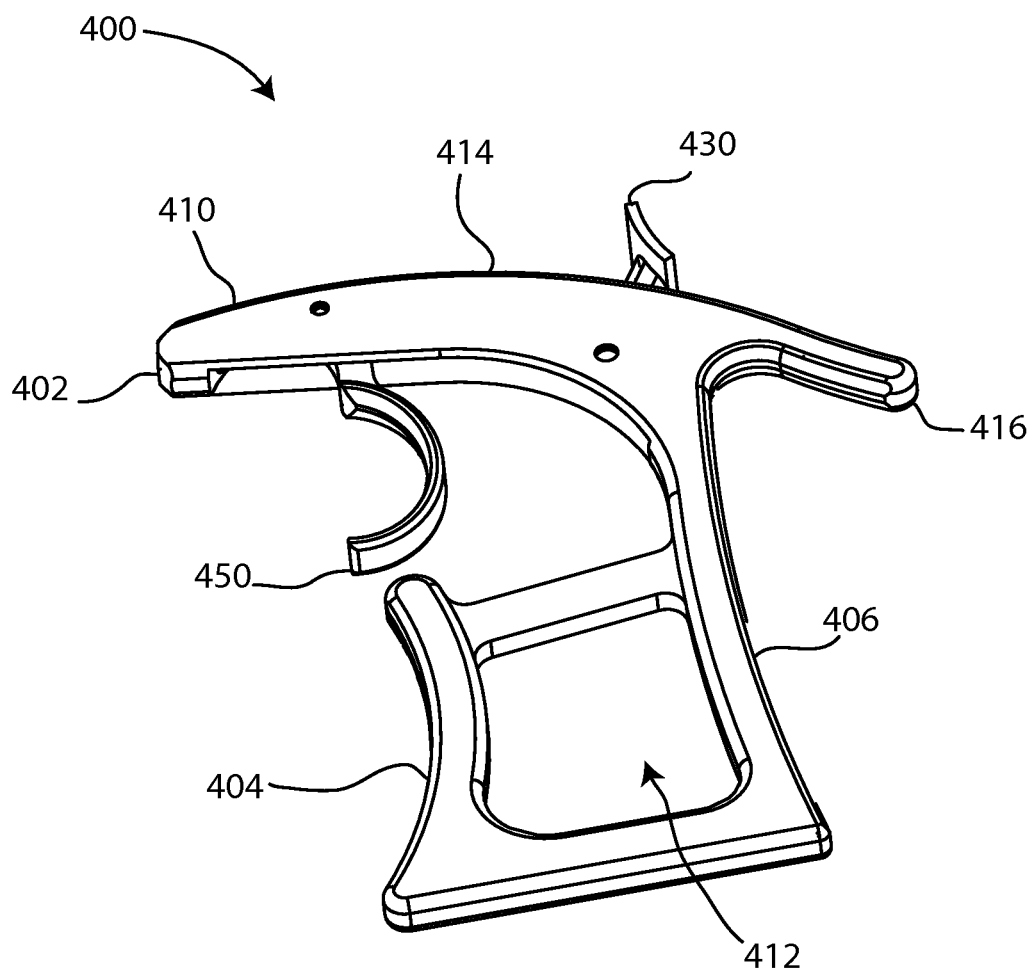
FIG. 14 is a bottom perspective view of the handle of FIG. 13.
Figure 15:
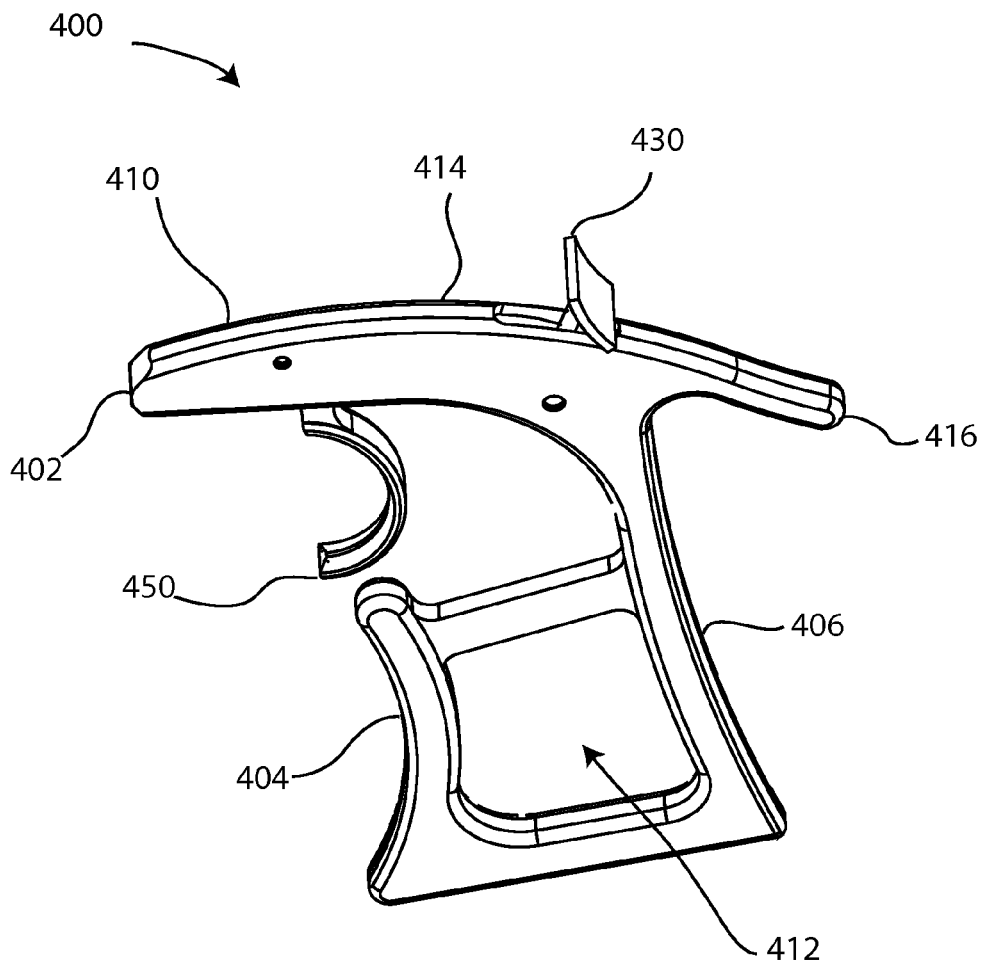
FIG. 15 is a top perspective view of the handle of FIG. 13.
Figure 16:
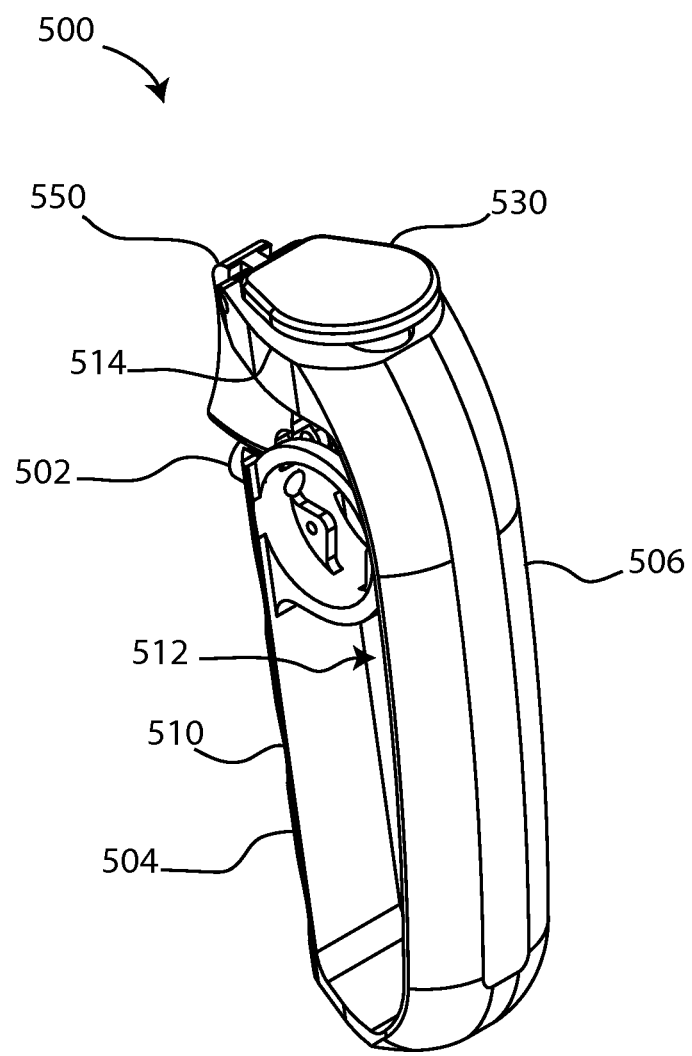
FIG. 16 is a side perspective view of yet another instrument handle.
Figure 17:
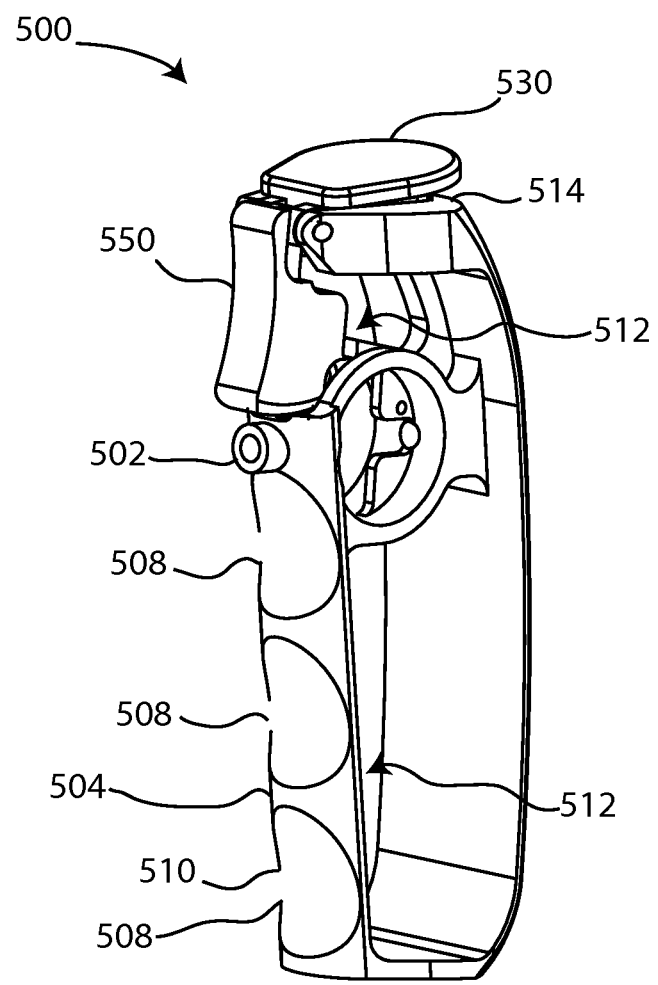
FIG. 17 is another side perspective view of the handle of FIG. 16.
Figure 18:
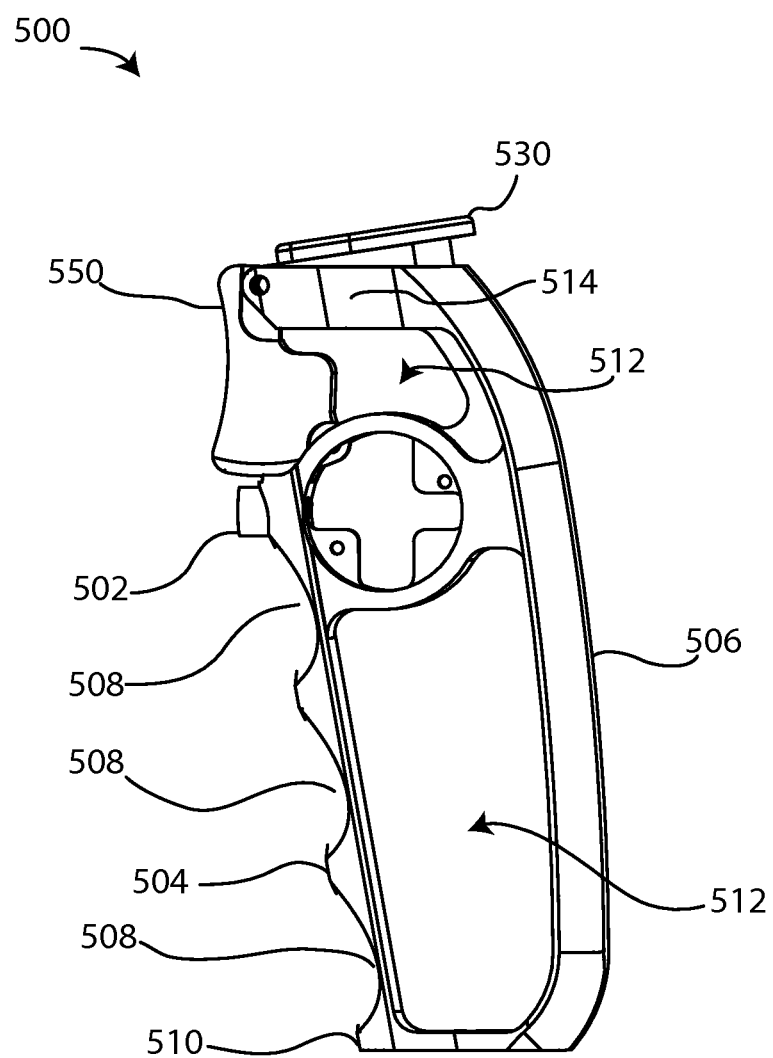
FIG. 18 is a side view of the handle of FIG. 16.
Figure 19:
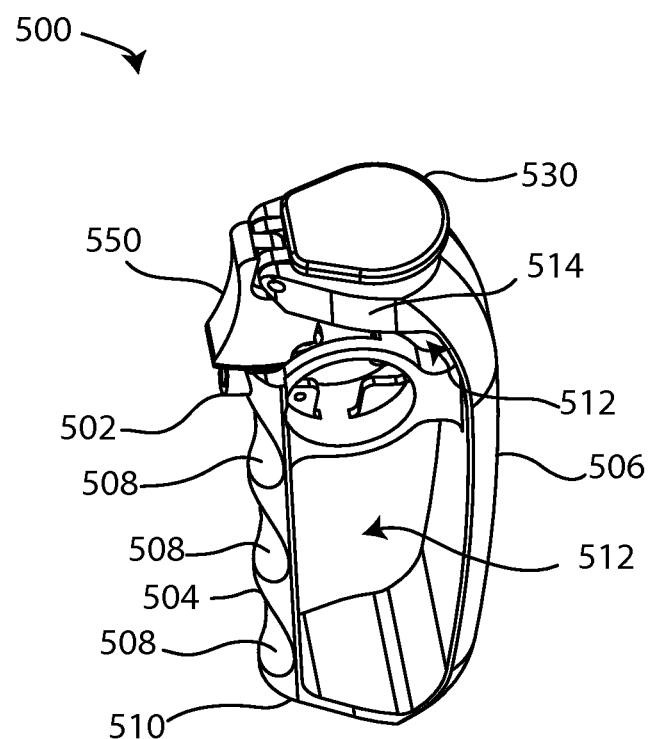
FIG. 19 is a top perspective view of the handle of FIG. 16.
Figure 20:
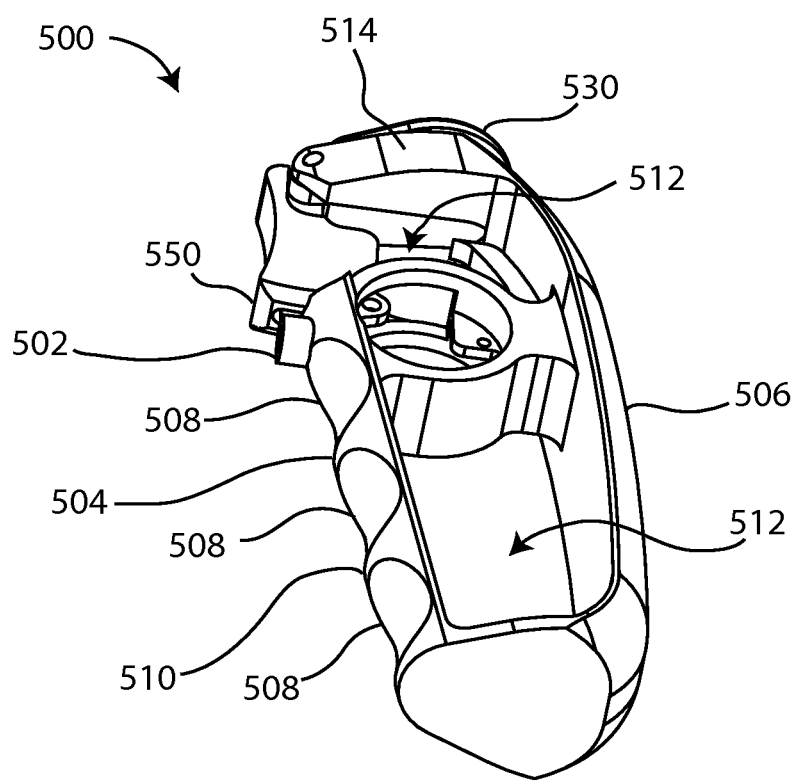
FIG. 20 is a bottom perspective view of the handle of FIG. 16.
Figure 21:
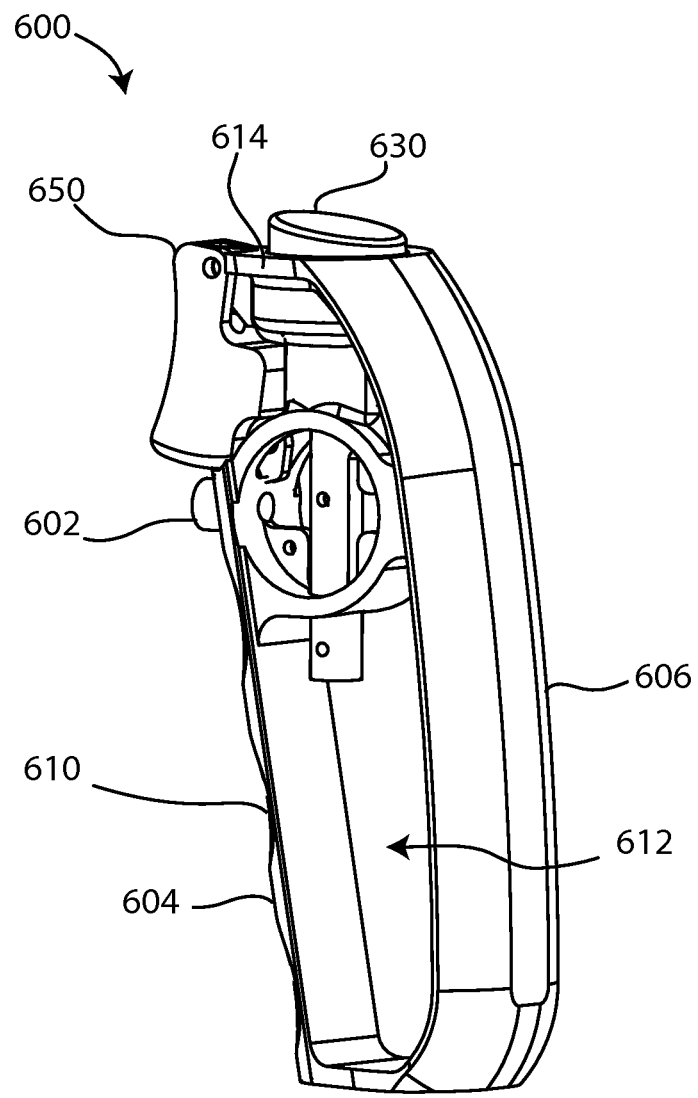
FIG. 21 is a side perspective view of yet another instrument handle.
Figure 22:
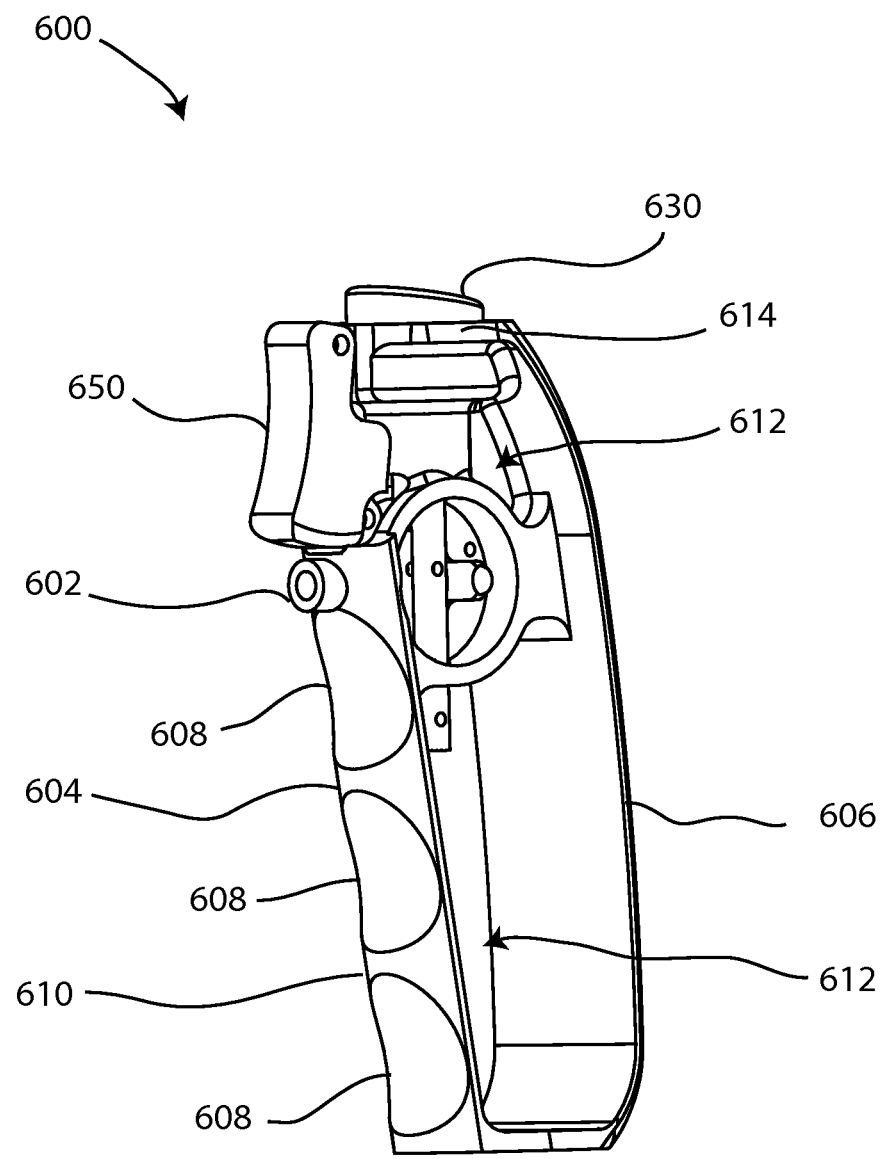
FIG. 22 is another side perspective view of the handle of FIG. 21.

Referring to FIGS. 13-15, an instrument handle 400 may include a frame 410, a first control 430, and a second control 450. Handle 400 may be bilaterally symmetric about a mid-sagittal plane like handle 100. Handle 400 may be operatively assembled to an operative component 10 to form a complete surgical instrument like handle 100. Handle 400 may be permanently or releasably coupled to operative component 10. Handle 400 may couple to any one of a plurality of different operative components 10.

Frame 410 may include a fitting 402, a body portion 414, a finger portion 404, and a palm portion 406. Body portion 414, finger portion 404, and palm portion 406 may be arranged around three sides of frame 410. Frame 410 may be bilaterally symmetric about the mid-sagittal plane of handle 400. Furthermore, fitting 402, body portion 414, finger portion 404, and palm portion 406 may each be bilaterally symmetric about the mid-sagittal plane of handle 400.

Fitting 402 may be described as a docking feature or connection feature to connect handle 400 to operative component 10. For example, fitting 402 may be a socket, a through hole, or a protrusion.

Body portion 414 may be described as a portion of the frame 410 which supports fitting 402, first control 430, and second control 450. Body portion 414 may extend generally in line with fitting 402. However, body portion 414 may extend in another orientation relative to fitting 402, such as oblique or transverse, in order to position a shaft 14 of an operative component 10 in a desired orientation relative to a user's hand, as described for handle 100.

Finger portion 404 may be described as a portion of the frame 410 for contacting one or more of the fingers of a human hand. Finger portion 404 may be transverse to body portion 414 near fitting 402. Finger portion 404 may include one or more indentations like handle 100. However, FIGS. 13-15 illustrate a finger portion 404 which is smooth, broad, and gently rounded. Finger portion 404 may also include one or more rests 416. FIGS. 13-15 illustrate a rest 416 which is sized, shaped, and positioned to fit the web between the thumb and index finger. The illustrated example of rest 416 is formed as an extended tail where the body portion 414 and the palm portion 406 meet. The indentations and/or rests 416 may increase the accuracy or security with which a user can grasp handle 400.

Palm portion 406 may be described as a portion of the frame 410 for contacting the palm of a human hand. For example, palm portion 406 may contact the palm or thenar eminence of a human hand. Palm portion 406 may extend transversely from body portion 414 opposite fitting 402 and generally parallel to finger portion 404. Palm portion 406 may connect to finger portion 404 opposite body portion 414.

Frame 410 may include one or more apertures 412 between body portion 414, finger portion 404, and palm portion 406. The embodiment of FIGS. 13-15 is shown with a large aperture 412 which hollows out a central portion of frame 410 so that body portion 414, finger portion 404, and palm portion 406 form a perimeter around the aperture 412. The apertures 412 may reduce the mass of frame 410, making the handle 400 lighter and easier to use for long periods of time. Reducing mass may decrease manufacturing costs by reducing the amount of material required to fabricate frame 410. Frame 410 may also be hollowed out in the vicinity of body portion 414, palm portion 406, and second control 450.

First control 430 and second control 450 may be described as actuators for first and second mechanisms, respectively, of a surgical instrument. First and second controls 430, 450 may share one, some, or all of the characteristics set forth for first control 130. First and second controls 430, 450 may embody different subsets of characteristics than first control 130. FIGS. 13-15 illustrate examples of first and second controls 430, 450. The illustrated first control 430 is a spring biased lever or trigger that protrudes obliquely from the body portion 414 opposite the finger and palm portions 404, 406 and at a distance from the fitting 402. The illustrated first control 430 is hinged to the body portion 414 near the intersection with palm portion 406 and is spring biased away from the body portion 414. The illustrated first control 430 is actuated by pressing the first control 430 forward toward the body portion 414, and automatically returns to the illustrated position when released. The illustrated second control 450 is a spring biased lever or trigger that protrudes transversely from the body portion 414 opposite first control 430 generally in line with finger portion 404 and at a distance from the fitting 402. The illustrated second control 450 and the finger portion 404 are on the same side of the fitting 402. The illustrated second control 450 is hinged to the body portion 414 and is spring biased toward the fitting 102. The illustrated second control 450 is actuated by pulling the second control 450 away from the fitting 402 with the index finger, and automatically returns to the illustrated position when released.

In use, handle 400 may be grasped by a human hand so that the palm portion 406 rests against the palm or thenar eminence; the finger portion 404 rests against the middle, ring, and little fingers with the web between the thumb and index finger adjacent to rest 416; the thumb rests on the first control 430; the index finger rests on the second control 450; and the fitting 402 is positioned beside the index finger so that a shaft 14 of an operative component may extend beside the index finger. In use, handle 400 is supported between the palm or thenar eminence and the middle, ring, and little fingers so that the index finger and thumb are free to operate the first and second controls 430, 450. Furthermore, it can be appreciated that, in use, handle 400 is substantially contained within the user's hand so that there is no projecting hardware other than the rest 416 and the operative component 10.

Handle 400 may rest in a user's hand in a square orientation so that the shaft 14 extends from the handle 400 generally parallel to the forearm of the user. The illustrated handle 400 may be suited to situations where the end effector 12 approaches the anatomy straight on. In other examples of handle 400, shaft 14 may extend obliquely or transversely relative to the forearm, as established by the orientation of body portion 414 to fitting 402.

Referring to FIGS. 16-20, an instrument handle 500 may include a frame 510, a first control 530, and a second control 550. Handle 500 may be bilaterally symmetric about a mid-sagittal plane like handle 100. Handle 500 may be operatively assembled to an operative component 10 to form a complete surgical instrument like handle 100. Handle 500 may be permanently or releasably coupled to operative component 10. Handle 500 may couple to any one of a plurality of different operative components 10.

Frame 510 may include a fitting 502, a body portion 514, a finger portion 504, and a palm portion 506. Body portion 514, finger portion 504, and palm portion 506 may be arranged around three sides of frame 510. Frame 510 may be bilaterally symmetric about the mid-sagittal plane of handle 500. Furthermore, fitting 502, body portion 514, finger portion 504, and palm portion 506 may each be bilaterally symmetric about the mid-sagittal plane of handle 500.

Fitting 502 may be described as a docking feature or connection feature to connect handle 500 to operative component 10. For example, fitting 502 may be a socket, a through hole as shown in FIGS. 16-20, or a protrusion.

Body portion 514 may be described as a portion of the frame 510 which supports first control 530 and second control 550. Body portion 514 may also support fitting 502. Body portion 514 may extend generally parallel to fitting 502. However, body portion 514 may extend in another orientation relative to fitting 502, such as oblique or transverse, in order to position a shaft 14 of an operative component 10 in a desired orientation relative to a user's hand, as described for handle 100.

Finger portion 504 may be described as a portion of the frame 510 for contacting one or more of the fingers of a human hand. Finger portion 504 may be transverse to body portion 514. Finger portion 504 may support fitting 502. Finger portion 504 may include one or more indentations 508 like handle 100. FIGS. 16-20 illustrate a finger portion 504 which has three indentations 508. Finger portion 504 may also include one or more rests, which may be finger rests, web rests, or thumb rests. However, FIGS. 16-20 illustrate a handle 500 without prominent rests. The indentations 508 and/or rests may increase the accuracy or security with which a user can grasp handle 500.

Palm portion 506 may be described as a portion of the frame 510 for contacting the palm of a human hand. For example, palm portion 506 may contact the palm or thenar eminence of a human hand. Palm portion 506 may extend transversely from body portion 514 opposite fitting 502 and generally parallel to finger portion 504. Palm portion 506 may connect to finger portion 504 opposite body portion 514.

Frame 510 may include one or more apertures 512 between body portion 514, finger portion 504, and palm portion 506. The embodiment of FIGS. 16-20 is shown with two apertures 512 which hollow out a central portion of frame 510 so that body portion 514, finger portion 504, and palm portion 506 form a perimeter around the apertures 512. The apertures 512 may reduce the mass of frame 510, making the handle 500 lighter and easier to use for long periods of time. Reducing mass may decrease manufacturing costs by reducing the amount of material required to fabricate frame 510.

First control 530 and second control 550 may be described as actuators for first and second mechanisms, respectively, of a surgical instrument. First and second controls 530, 550 may share one, some, or all of the characteristics set forth for first control 130. First and second controls 530, 550 may embody different subsets of characteristics than first control 130. FIGS. 16-20 illustrate examples of first and second controls 530, 550. The illustrated first control 530 is a spring biased lever or trigger that protrudes obliquely from the body portion 514 opposite the finger and palm portions 504, 506. The illustrated first control 530 is hinged to the front of body portion 514 near the intersection with finger portion 504 and is spring biased away from the body portion 514. The illustrated first control 530 is actuated by pressing the first control 530 down toward the body portion 514, and automatically returns to the illustrated position when released. The illustrated second control 550 is a spring biased lever or trigger that protrudes transversely from the body portion 514 opposite first control 530 generally in line with finger portion 504. The illustrated second control 550 and the finger portion 504 are on opposite sides of the fitting 502. The illustrated second control 550 is hinged to the front of body portion 514 and is spring biased toward the fitting 102, i.e., the front of body portion 514. FIGS. 16-20 illustrate an arrangement in which the first and second controls 530, 550 share a single hinge. The illustrated second control 550 is actuated by pulling the second control 550 back from the fitting 502 with the index finger, and automatically returns to the illustrated position when released.

In use, handle 500 may be grasped by a human hand so that the palm portion 506 rests against the palm or thenar eminence; the middle, ring, and little fingers rest against the finger portion 504 in the indentations 508; the thumb rests on the first control 530; the index finger rests on the second control 550; and the fitting 502 is positioned between the index and middle fingers so that a shaft 14 of an operative component may extend between the index and middle fingers. In use, handle 500 is supported between the palm or thenar eminence and the middle, ring, and little fingers so that the index finger and thumb are free to operate the first and second controls 530, 550. Furthermore, it can be appreciated that, in use, handle 500 is completely contained within the user's hand so that there is no projecting hardware other than the operative component 10.

Handle 500 may rest in a user's hand in an upright orientation. Handle 500 may also be suited to situations where the end effector 12 approaches the anatomy straight on. In other examples of handle 500, shaft 14 may extend obliquely or transversely relative to the forearm, as established by the orientation of body portion 514 to fitting 502. It can also be appreciated that handle 500 may be favorably adapted for a user having a smaller grip span.

Referring to FIGS. 21-26, an instrument handle 600 may include a frame 610, a first control 630, and a second control 650. Handle 600 may be bilaterally symmetric about a mid-sagittal plane like handle 100. Handle 600 may be operatively assembled to an operative component 10 to form a complete surgical instrument like handle 100. Handle 600 may be permanently or releasably coupled to operative component 10. Handle 600 may couple to any one of a plurality of different operative components 10.

Frame 610 may include a fitting 602, a body portion 614, a finger portion 604, and a palm portion 606. Body portion 614, finger portion 604, and palm portion 606 may be arranged around three sides of frame 610. Frame 610 may be bilaterally symmetric about the mid-sagittal plane of handle 600. Furthermore, fitting 602, body portion 614, finger portion 604, and palm portion 606 may each be bilaterally symmetric about the mid-sagittal plane of handle 600.

Fitting 602 may be described as a docking feature or connection feature to connect handle 600 to operative component 10. For example, fitting 602 may be a socket, a through hole as shown in FIGS. 21-26, or a protrusion.

Body portion 614 may be described as a portion of the frame 610 which supports first control 630 and second control 650. Body portion 614 may also support fitting 602. Body portion 614 may extend generally parallel to fitting 602. However, body portion 614 may extend in another orientation relative to fitting 602, such as oblique or transverse, in order to position a shaft 14 of an operative component 10 in a desired orientation relative to a user's hand, as described for handle 100.

Finger portion 604 may be described as a portion of the frame 610 for contacting one or more of the fingers of a human hand. Finger portion 604 may be transverse to body portion 614. Finger portion 604 may support fitting 602. Finger portion 604 may include one or more indentations 608 like handle 100. FIGS. 21-26 illustrate a finger portion 604 which has three indentations 608. Finger portion 604 may also include one or more rests, which may be finger rests, web rests, or thumb rests. However, FIGS. 21-26 illustrate a handle 600 without prominent rests. The indentations 608 and/or rests may increase the accuracy or security with which a user can grasp handle 600.

Palm portion 606 may be described as a portion of the frame 610 for contacting the palm of a human hand. For example, palm portion 606 may contact the palm or thenar eminence of a human hand. Palm portion 606 may extend transversely from body portion 614 opposite fitting 602 and generally parallel to finger portion 604. Palm portion 606 may connect to finger portion 604 opposite body portion 614.

Frame 610 may include one or more apertures 612 between body portion 614, finger portion 604, and palm portion 606. The embodiment of FIGS. 21-26 is shown with two apertures 612 which hollow out a central portion of frame 610 so that body portion 614, finger portion 604, and palm portion 606 form a perimeter around the apertures 612. The apertures 612 may reduce the mass of frame 610, making the handle 600 lighter and easier to use for long periods of time. Reducing mass may decrease manufacturing costs by reducing the amount of material required to fabricate frame 610.

Figure 23:
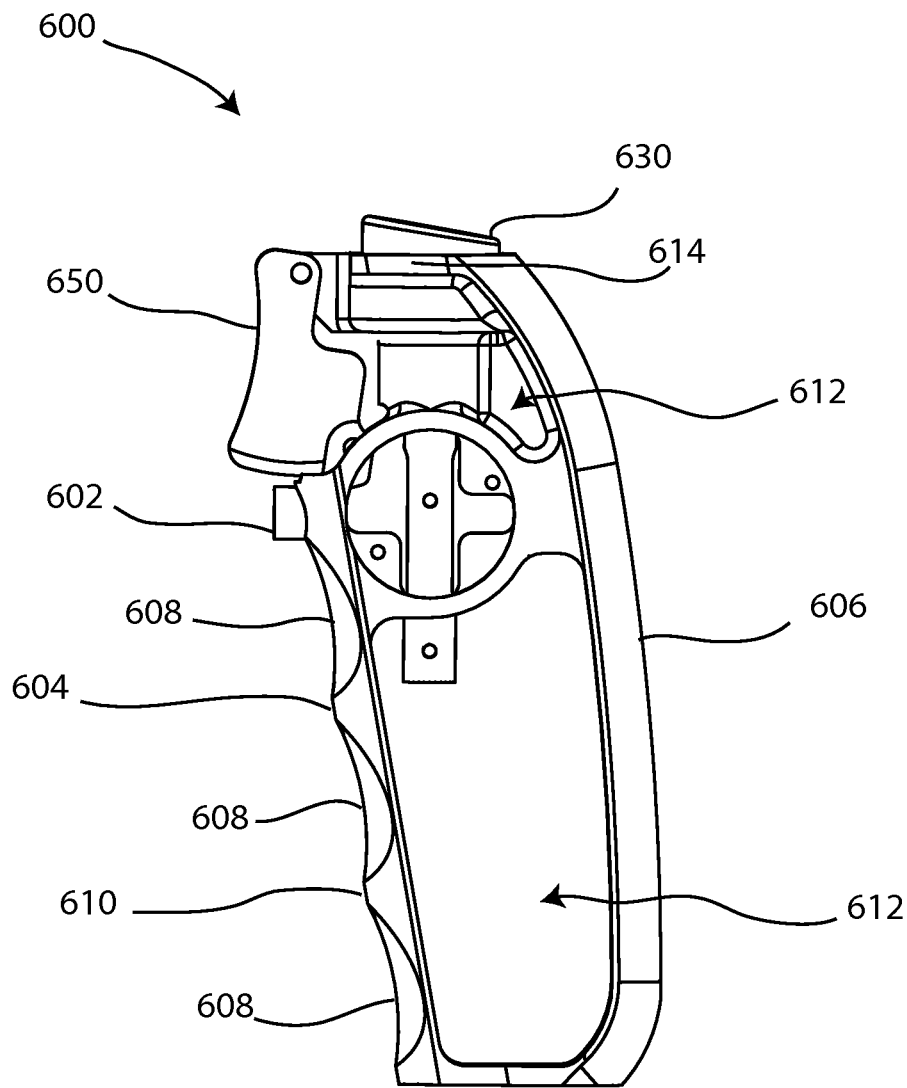
FIG. 23 is a side view of the handle of FIG. 21.
Figure 24:
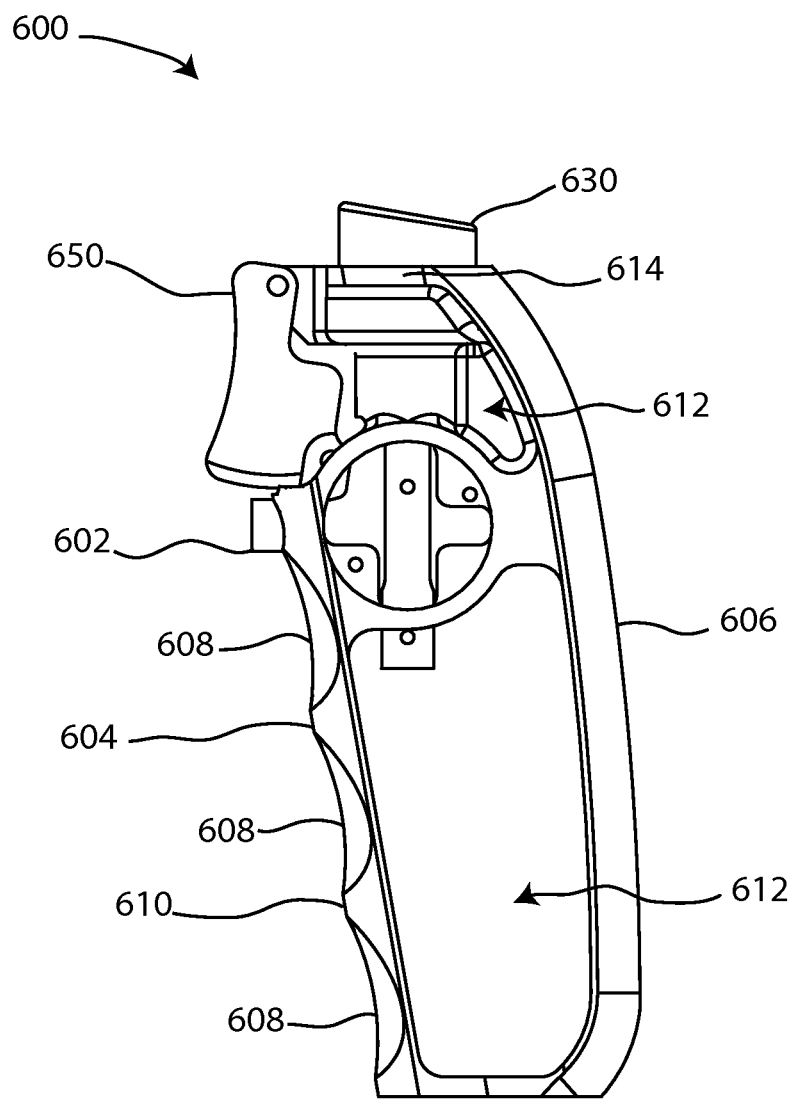
FIG. 24 is another side view of the handle of FIG. 21.
Figure 25:
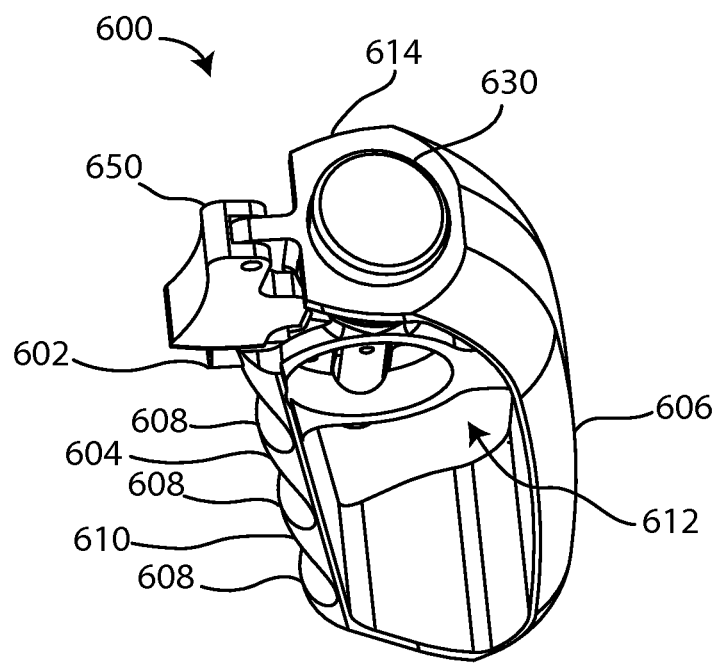
FIG. 25 is a top perspective view of the handle of FIG. 21.
Figure 26:
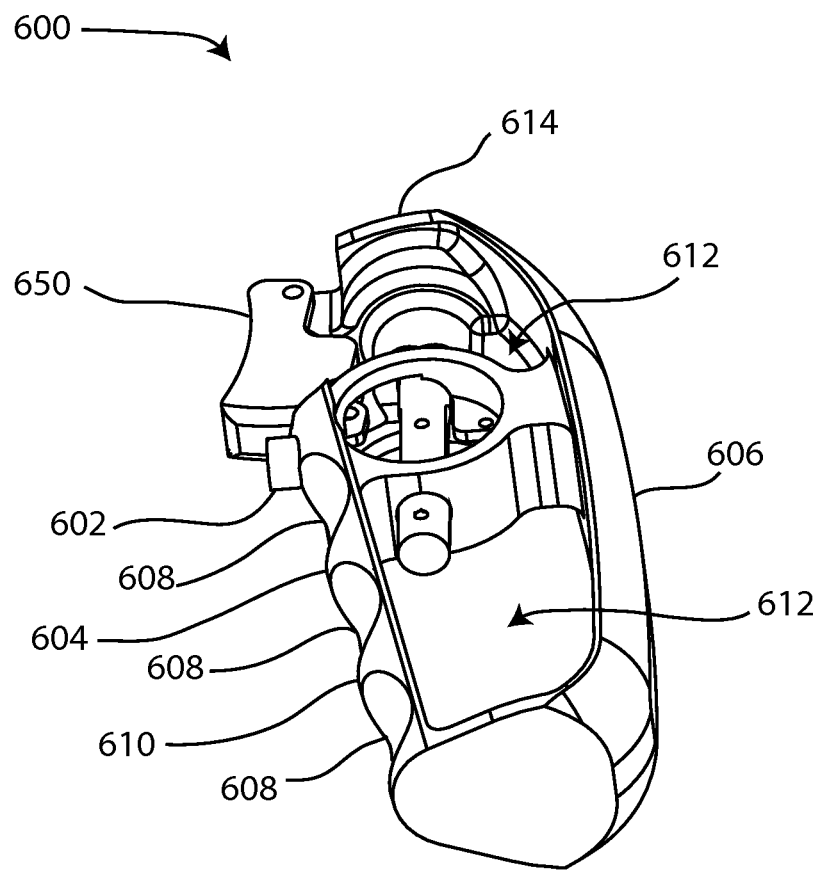
FIG. 26 is a bottom perspective view of the handle of FIG. 21.

First control 630 and second control 650 may be described as actuators for first and second mechanisms, respectively, of a surgical instrument. First and second controls 630, 650 may share one, some, or all of the characteristics set forth for first control 130. First and second controls 630, 650 may embody different subsets of characteristics than first control 130. FIGS. 21-26 illustrate examples of first and second controls 630, 650. The illustrated first control 630 is a spring biased plunger that protrudes transversely from the body portion 614 opposite the finger and palm portions 604, 606. The illustrated first control 630 is mounted to the body portion 614 between finger portion 604 and palm portion 606, and is spring biased to protrude from the body portion 614. The illustrated first control 630 is actuated by pressing the first control 630 down toward the body portion 614. First control 630 may automatically return to the protruding position when released. Alternately, first control 630 may remain in the depressed position until depressed again, at which point first control may return to the protruding position. FIGS. 23-24 show first control 630 in the protruding and depressed positions. The illustrated second control 650 is a spring biased lever or trigger that protrudes transversely from the body portion 614 opposite first control 630 generally in line with finger portion 604. The illustrated second control 650 and the finger portion 604 are on opposite sides of the fitting 602. The illustrated second control 650 is hinged to the front of body portion 614 and is spring biased toward the fitting 102, i.e., the front of body portion 614. The illustrated second control 650 is actuated by pulling the second control 650 back from the fitting 602 with the index finger, and automatically returns to the illustrated position when released.

In use, handle 600 may be grasped by a human hand so that the palm portion 606 rests against the palm or thenar eminence; the middle, ring, and little fingers rest against the finger portion 604 in the indentations 608; the thumb rests on the first control 630; the index finger rests on the second control 650; and the fitting 602 is positioned between the index and middle fingers so that a shaft 14 of an operative component may extend between the index and middle fingers. In use, handle 600 is supported between the palm or thenar eminence and the middle, ring, and little fingers so that the index finger and thumb are free to operate the first and second controls 630, 650. Furthermore, it can be appreciated that, in use, handle 600 is completely contained within the user's hand so that there is no projecting hardware other than the operative component 10.

It can be appreciated that handle 600 may rest in a user's hand in an upright orientation. Handle 600 may also be suited to situations where the end effector 12 approaches the anatomy straight on. In other examples of handle 600, shaft 14 may extend obliquely or transversely relative to the forearm, as established by the orientation of body portion 614 to fitting 602. It can also be appreciated that handle 600 may be favorably adapted for a user having a smaller grip span.

Figure 27:
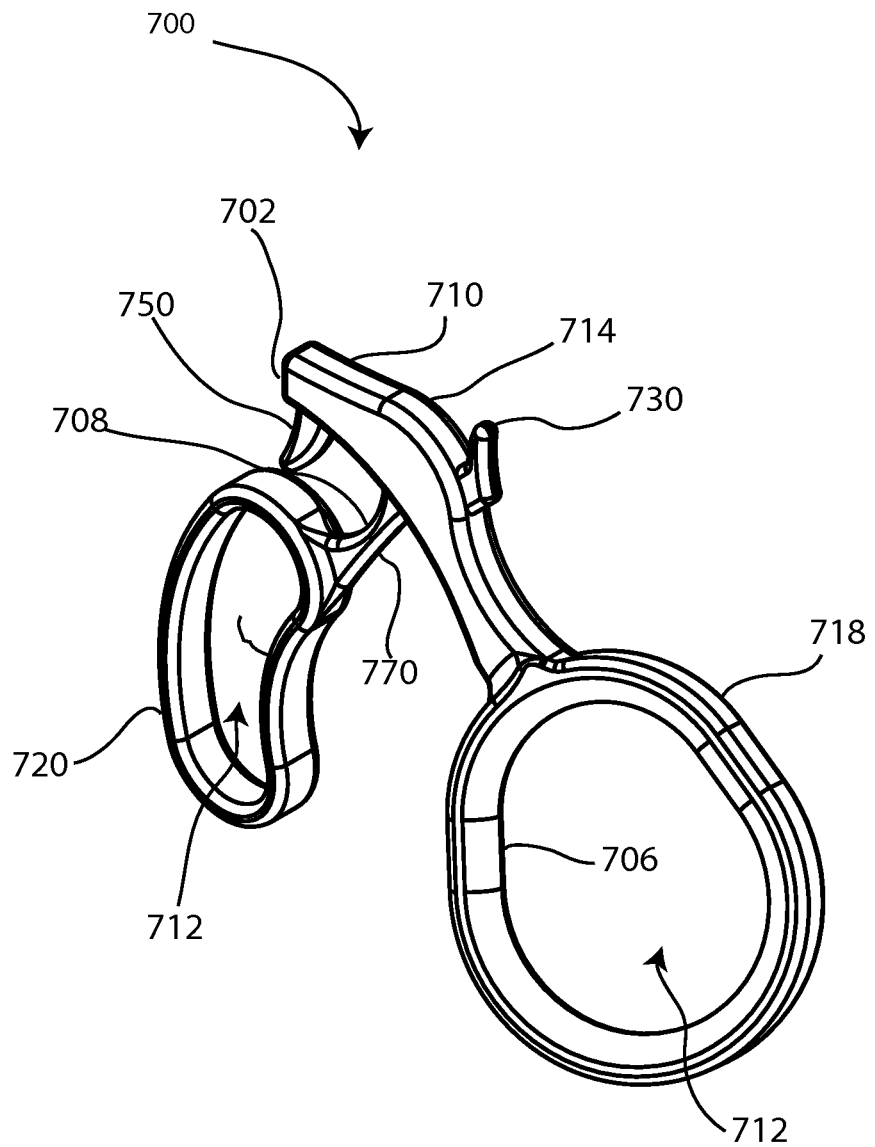
FIG. 27 is a side perspective view of yet another instrument handle.

Referring to FIG. 27, an instrument handle 700 may include a frame 710, an arm 770, a first control 730, and a second control 750. One or more portions of handle 700 may be bilaterally symmetric about a mid-sagittal plane. Handle 700 may be operatively assembled to an operative component 10 to form a complete surgical instrument like handle 100. Handle 700 may be permanently or releasably coupled to operative component 10. Handle 700 may couple to any one of a plurality of different operative components 10.

Frame 710 may include a fitting 702, a body portion 714, and a palm portion 706. One or more portions of frame 710 may be bilaterally symmetric about the mid-sagittal plane of handle 700. Furthermore, fitting 702, body portion 714, and palm portion 706 may each be bilaterally symmetric about the mid-sagittal plane of handle 700.

Fitting 702 may be described as a docking feature or connection feature to connect handle 700 to operative component 10. For example, fitting 702 may be a socket, a through hole, or a protrusion.

Body portion 714 may be described as a portion of the frame 710 which supports fitting 702, arm 770, first control 730, and second control 750. Body portion 714 may extend generally parallel to fitting 702. However, body portion 714 may extend in another orientation relative to fitting 702, such as oblique or transverse, in order to position a shaft 14 of an operative component 10 in a desired orientation relative to a user's hand, as described for handle 100.

Palm portion 706 may be described as a portion of the frame 710 for contacting the palm of a human hand. For example, palm portion 706 may contact the palm or thenar eminence of a human hand. Palm portion 706 may extend obliquely from body portion 714 opposite fitting 702. In the illustrated embodiment, palm portion 706 is a portion of an inner surface of a loop 718 which is sized, shaped, and positioned to encircle the base of a thumb of a human hand. Alternately, palm portion 706 may resemble other palm portions disclosed herein.

Frame 710 may include one or more apertures 712. The embodiment of FIG. 27 is shown with an aperture 712 which hollows out a central portion of loop 718. The aperture 712 may reduce the mass of frame 710, making the handle 700 lighter and easier to use for long periods of time. Reducing mass may decrease manufacturing costs by reducing the amount of material required to fabricate frame 710.

Arm 770 may be described as a projection from frame 710. Arm 770 may extend obliquely from body portion 714 near fitting 702, and may extend obliquely relative to palm portion 706 as well. Arm 770 may be fixed or movable relative to frame 710. For example, arm 770 may be integrally formed with, welded to, or fastened to frame 710. In another example, arm 770 may be hinged to frame 710 so that arm 770 may be positioned relatively closer to, or farther from, palm portion 706. If movable, arm 770 may also be biased to remain in a nominal position unless actuated by a user. If movable, arm 770 may further be described as an actuator for a mechanism of a surgical instrument, as will be discussed below. Arm may include a finger portion 704.

Finger portion 704 may be described as a portion of arm 770 for contacting one or more of the fingers of a human hand. Finger portion 704 may extend obliquely relative to body portion 714. Finger portion 704 may include one or more indentations 708 like handle 100. However, FIG. 27 illustrates a finger portion 704 which is smooth, broad, and gently rounded. Finger portion 704 may also include one or more rests, which may be finger rests, web rests, or thumb rests. However, FIG. 27 illustrates a handle 700 without prominent rests. The indentations and/or rests may increase the accuracy or security with which a user can grasp handle 700. In the illustrated embodiment, finger portion 704 is a portion of an inner surface of a loop 720 which is sized, shaped, and positioned to encircle the ulnar three fingers of a human hand.

Arm 770 may include one or more apertures 712. The embodiment of FIG. 27 is shown with an aperture 712 which hollows out a central portion of loop 720. The aperture 712 may reduce the mass of arm 770, making the handle 700 lighter and easier to use for long periods of time. Reducing mass may decrease manufacturing costs by reducing the amount of material required to fabricate arm 770.

First control 730 and second control 750 may be described as actuators for first and second mechanisms, respectively, of a surgical instrument. First and second controls 730, 750 may share one, some, or all of the characteristics set forth for first control 130. First and second controls 730, 750 may embody different subsets of characteristics than first control 130. FIG. 27 illustrates examples of first and second controls 730, 750. The illustrated first control 730 is a spring biased lever or trigger that protrudes transversely from the body portion 714 opposite the finger and palm portions 704, 706. The illustrated first control 730 is mounted to the body portion 714 between fitting 702 and palm portion 706, and may be spring biased toward the rear of body portion 714. Alternately, first control 730 may be biased toward the front of body portion 714, i.e., toward fitting 702. In another alternative, first control 730 may be biased to a middle position and movable forward and backward relative to the body portion 714. The illustrated first control 730 may be actuated by pressing the first control 730 forward toward the fitting 702 or by pulling the first control 730 backward away from the fitting 702. First control 730 may automatically return to the nominal biased position when released. Alternately, first control 730 may remain in the forward or backward position until pressed again, at which point first control may return to the nominal position. The illustrated second control 750 is a spring biased lever or trigger that protrudes transversely from the body portion 714 opposite first control 730 near fitting 702 and finger portion 704. The illustrated second control 750 and the finger portion 704 are on the same side of the fitting 702. The illustrated second control 750 is hinged to the front of body portion 714 and is spring biased toward the fitting 102, i.e., the front of body portion 714. The illustrated second control 750 is actuated by pulling the second control 750 back from the fitting 702 with the index finger, and automatically returns to the illustrated position when released.

In use, handle 700 may be grasped by a human hand so that the palm portion 706 rests against the palm or thenar eminence with the thumb protruding through the loop 718; the middle, ring, and little fingers rest against the finger portion 704 with the middle, ring, and little fingers protruding through the loop 720; the thumb rests on the first control 730; the index finger rests on the second control 750; and the fitting 702 is positioned beside the index finger so that a shaft 14 of an operative component may extend beside the index finger. In use, handle 700 may be supported by the palm or thenar eminence alone so that the fingers and thumb are free to operate a movable embodiment of the arm 770, the first control 730, and the second control 750. Handle 700 may also be at least partially supported by the middle, ring, and little fingers on a fixed or movable embodiment of the arm 770 so that the index finger and thumb are free to operate the first and second controls 730, 750.

While the illustrated handle 700 may rest in a user's hand so that the shaft 14 extends from the handle 700 generally parallel to the forearm of the user, in other examples of handle 700, shaft 14 may extend obliquely or transversely relative to the forearm, as established by the orientation of body portion 714 to fitting 702.

In other examples of handles according to the present disclosure, only one control may be provided. In still other examples, more than two controls may be provided. In other examples, one or more of the controls may be replaced with static features that serve as additional rests. For example, first control 130 of handle 100 may be replaced with a static rest so that the index finger may be used to further stabilize the handle 100 in use. Any handle within the scope of the present disclosure may be further modified by including a web rest like rest 416, or a thumb rest.

Handles according to the present disclosure may be fabricated from metal, polymer, ceramic, elastomer, wood, glass, composite material, and combinations thereof. A single handle, or a single component part of a handle, may be fabricated from a combination of materials in order to provide an appropriate material for each feature of the handle or part.

Handles of the present disclosure may be configured for unlimited repeated use, limited repeated use, or single use. Handles for unlimited repeated use may be designed more robustly and may be made from materials that are less susceptible to wear, corrosion, bending, cracking, or breaking. Handles for unlimited repeated use in a surgical setting may also be designed for easy cleaning and for repeated steam sterilization. Handles for single use may be designed to minimize cost of goods by selecting economical materials, fabrication methods, manufacturing processes, inspection methods, and tooling. For example, a single-use handle may incorporate an over-molded handle and an inner machined core, where the core is fabricated in a single set-up on a high-speed machine tool center. Single-use handles may have no provision for cleaning or sterilization. Single-use handles may also incorporate materials that degrade during steam sterilization, for example as a deterrent to off-label reuse.

The handles set forth in the present disclosure may be provided in a kit which includes several different handle styles. The kit may include several versions of a single handle style, each with a different orientation of body portion to fitting. The kit may include different handle styles and different orientations of body portion to fitting.

The handles of the present disclosure may also be provided in a kit which includes several different operative components. For example, the operative components may differ in the types of end effectors provided, the shaft configuration (straight, bent, twisted), shaft length.

Any of the kits may be presented in a case or tray which organizes and positions the contents for easy selection and use. For example, a case may hold a selection of handles so that a user may select and grasp the handle in the proper functional orientation in one motion. In another example, a case may hold a selection of operative components so that a user may couple or decouple a handle and a selected operative component without releasing the user's functional grasp of the handle.

While the present disclosure has been made in the context of handles for surgical instruments, the systems and methods described herein may have a broad range of applications beyond the fields of surgery or medical devices.

It should be understood that the present components, systems, kits, apparatuses, and methods are not intended to be limited to the particular forms disclosed. Rather, they are intended to include all modifications, equivalents, and alternatives falling within the scope of the claims. They are further intended to include embodiments which may be formed by combining features from the disclosed embodiments.

The claims are not to be interpreted as including means-plus- or step-plus-function limitations, unless such a limitation is explicitly recited in a given claim using the phrase(s) "means for" or "step for," respectively.

The term "coupled" is defined as connected, although not necessarily directly, and not necessarily mechanically.

The use of the word "a" or "an" when used in conjunction with the term "comprising" in the claims and/or the specification may mean "one," but it is also consistent with the meaning of "one or more" or "at least one." The term "about" means, in general, the stated value plus or minus 5%. The use of the term "or" in the claims is used to mean "and/or" unless explicitly indicated to refer to alternatives only or the alternative are mutually exclusive, although the disclosure supports a definition that refers to only alternatives and "and/or."

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements, possesses those one or more steps or elements, but is not limited to possessing only those one or more elements. Likewise, a step of a method or an element of a device that "comprises," "has," "includes" or "contains" one or more features, possesses those one or more features, but is not limited to possessing only those one or more features. Furthermore, a device or structure that is configured in a certain way is configured in at least that way, but may also be configured in ways that are not listed.

The invention claimed is:

1. An instrument adapted for use by a human hand, the instrument comprising:
    an end effector, wherein the end effector comprises a working segment and a connection segment opposite the working segment, wherein the connection segment of the end effector comprises a center longitudinal axis; and
    a handle extending from the connection segment of the end effector, the handle comprising:
    a first control;
    wherein the handle is configured to be supported between a thenar eminence of the hand and at least one support digit of the hand, wherein the at least one support digit is selected from the group consisting of a middle finger, a ring finger, and a little finger of the hand;
    wherein the first control is configured to be actuated by a first actuation digit of the hand, wherein the first actuation digit is selected from the group consisting of an index finger and a thumb of the hand;
    wherein the working segment of the end effector is positioned and oriented to perform a first action on a selected portion of a workpiece when the first control is actuated;
    wherein, when the handle is supported between the thenar eminence and the at least one support digit, the first control is on an opposite side of the center longitudinal axis of the connection segment from the at least one support digit, the first actuation digit rests on the first control, and a wrist, an elbow, and a shoulder corresponding to the hand are all in neutral positions.

2. The instrument of claim 1, wherein the handle is bilaterally symmetric about a mid-sagittal plane, wherein the handle comprises a fitting, wherein the fitting carries the connection segment of the end effector.

3. The instrument of claim 2, wherein the fitting carries the connection segment with the axis parallel to the mid-sagittal plane.

4. The instrument of claim 2, wherein the fitting carries the connection segment with the axis at an angle to the mid-sagittal plane.

5. The instrument of claim 2, wherein the working segment of the end effector comprises a functional plane, wherein the fitting carries the connection segment with the functional plane parallel to the mid-sagittal plane.

6. The instrument of claim 2, wherein the working segment of the end effector comprises a functional plane, wherein the fitting carries the connection segment with the functional plane at a first angle to the mid-sagittal plane.

7. The instrument of claim 6, wherein the fitting carries the connection segment with the functional plane at a second angle to the mid-sagittal plane.

8. An instrument adapted for use by a human hand, the instrument comprising:
 an end effector, wherein the end effector comprises a working segment and a connection segment opposite the working segment, wherein the connection segment of the end effector comprises a center longitudinal axis; and
 a handle extending from the connection segment of the end effector, the handle comprising:
 a fitting, wherein the fitting carries the connection segment of the end effector;
 a first control; and
 a frame, wherein the frame carries the fitting and the first control;
 wherein the handle is configured to be supported between a thenar eminence of the hand and at least one support digit of the hand, wherein the at least one support digit is selected from the group consisting of a middle finger, a ring finger, and a little finger of the hand;
 wherein the first control is configured to be actuated by a first actuation digit of the hand, wherein the first actuation digit is selected from the group consisting of an index finger and a thumb of the hand;
 wherein the working segment of the end effector performs a first action when the first control is actuated;
 wherein, when the handle is supported between the thenar eminence and the at least one support digit, the first control is on an opposite side of the center longitudinal axis of the connection segment from the at least one support digit, and the first actuation digit rests on the first control.

9. The instrument of claim 8, wherein the fitting is between the middle finger and the index finger when the handle is supported between the thenar eminence and the at least one support digit.

10. The instrument of claim 8, wherein the fitting is between the index finger and the thumb when the handle is supported between the thenar eminence and the at least one support digit.

11. The instrument of claim 8, wherein the handle comprises:
 a body portion, wherein the body portion comprises a front segment and a rear segment opposite the front segment, wherein the front segment carries the fitting, wherein the rear segment carries the first control;
 a palm portion extending transversely from the rear segment, wherein the palm portion is configured to be supported by the thenar eminence; and
 a finger portion extending beside the palm portion near the front segment, wherein the finger portion is configured to be supported by the at least one support digit.

12. The instrument of claim 8, wherein the handle comprises:
 a second control, wherein the frame carries the second control;
 wherein the second control is configured to be actuated by a second actuation digit of the hand, wherein the second actuation digit is a remaining digit in the group consisting of an index finger and a thumb of the hand after selection of the first actuation digit;
 wherein the working segment of the end effector performs a second action when the second control is actuated;
 wherein, when the handle is supported between the thenar eminence and the at least one support digit, the second actuation digit rests on the second control.

13. The instrument of claim 12, wherein the second control and the finger portion are on opposite sides of the center longitudinal axis of the connection segment.

14. The instrument of claim 12, wherein the second control and the finger portion are on the same side of the center longitudinal axis of the connection segment.

15. An instrument handle adapted for use by a human hand, the handle comprising:
 an end effector, wherein the end effector comprises a working segment and a connection segment opposite the working segment, wherein the connection segment of the end effector comprises a center longitudinal axis;
 a fitting extending from the connection segment of the end effector;
 a body portion, wherein the body portion comprises a first control and a second control, wherein the first and second controls are configured to be actuated by first and second actuation digits of the hand, respectively, wherein the first and second actuation digits are selected from the group consisting of the index finger and the thumb of the hand;
 a palm portion extending transversely from the body portion, wherein the palm portion is configured to be supported by a thenar eminence of the hand; and
 a finger portion spaced apart from the palm portion, wherein the finger portion is configured to be supported by at least one support digit of the hand, wherein the at least one support digit is selected from the group consisting of a middle finger, a ring finger, and a little finger of the hand;
 wherein the first control is on an opposite side of the center longitudinal axis of the connection segment from the finger portion.

16. The handle of claim 15, wherein the fitting is between the finger portion and the first and second controls, wherein the fitting is between the middle finger and the index finger when the palm portion is supported by the thenar eminence and the finger portion is supported by the at least one support digit.

17. The handle of claim 16, wherein the body portion carries the fitting.

18. The handle of claim 16, wherein the finger portion carries the fitting.

19. The handle of claim 15, wherein the fitting is between the first and second controls, wherein the fitting is between the index finger and the thumb when the palm portion is supported by the thenar eminence and the finger portion is supported by the at least one support digit.

20. The handle of claim 19, wherein the finger portion comprises a third control, wherein the third control is configured to be actuated by at least one of the support digits.

* * * * *